United States Patent
Zhang et al.

(10) Patent No.: US 11,111,192 B2
(45) Date of Patent: Sep. 7, 2021

(54) METHODS AND SYSTEMS FOR PRODUCING PARA-XYLENE FROM C8-CONTAINING COMPOSITIONS

(71) Applicant: Saudi Arabian Oil Company, Dhahran (SA)

(72) Inventors: Zhonglin Zhang, Dhahran (SA); Sohel K Shaikh, Dhahran (SA); Veera Venkata R Tammana, Dhahran (SA); Raed H. Abudawoud, Khobar (SA); Bruce Richard Beadle, Dhahran (SA); Hisham Tawfiq Bassam, Al Khubar (SA); Rakan Sulaiman Bilaus, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/936,904

(22) Filed: Jul. 23, 2020

(65) Prior Publication Data
US 2020/0354289 A1    Nov. 12, 2020

Related U.S. Application Data

(63) Continuation of application No. 16/282,408, filed on Feb. 22, 2019, now Pat. No. 10,843,983.

(51) Int. Cl.
  *B01J 8/00* (2006.01)
  *C07C 5/22* (2006.01)
  (Continued)

(52) U.S. Cl.
  CPC ............. *C07C 5/2732* (2013.01); *B01J 8/009* (2013.01); *B01J 16/005* (2013.01); *B01J 19/245* (2013.01);
  (Continued)

(58) Field of Classification Search
  None
  See application file for complete search history.

(56) References Cited

U.S. PATENT DOCUMENTS

| | | | |
|---|---|---|---|
| 4,101,595 A | 7/1978 | Chen et al. | |
| 5,705,726 A | 1/1998 | Abichandani et al. | |
| (Continued) | | | |

FOREIGN PATENT DOCUMENTS

WO     2016097855 A1    6/2016

OTHER PUBLICATIONS

Koh, "Reverse osmosis molecular differentiation of organic liquids using carbon molecular sieve membranes", Report, Aug. 19, 2016, vol. 353 Issue 6301, sciencemag.org.
(Continued)

*Primary Examiner* — Jennifer A Leung
(74) *Attorney, Agent, or Firm* — Dinsmore & Shohl LLP

(57) ABSTRACT

A method for producing para-xylene (PX) includes introducing a $C_8$ aromatic-containing composition to a xylene rerun column to separate the $C_8$ aromatic-containing composition into a xylene-containing effluent and a heavy effluent and passing the xylene-containing effluent to a PX processing loop that includes a PX recovery unit operable to separate a PX product from the xylene-containing effluent, a membrane isomerization unit operable to convert a portion of the MX, OX, or both from the xylene-containing effluent to PX, an EB dealkylation unit operable to dealkylate EB from the xylene-containing effluent to produce benzene, toluene, and other $C_{7-}$ compounds, and a membrane separation unit operable to produce a permeate that is PX-rich and a retentate that is PX-lean. The permeate is passed to the PX recovery unit for recovery of PX, which the retentate is bypassed around the PX recovery unit circulated through the xylene processing loop.

13 Claims, 6 Drawing Sheets

(51) Int. Cl.
*C07C 7/144* (2006.01)
*C07C 15/08* (2006.01)
*C07C 5/27* (2006.01)
*B01J 16/00* (2006.01)
*B01J 19/24* (2006.01)
*C07C 7/00* (2006.01)
*C07C 7/12* (2006.01)
*C07C 7/14* (2006.01)

(52) U.S. Cl.
CPC ............. *B01J 19/2475* (2013.01); *C07C 5/22* (2013.01); *C07C 5/277* (2013.01); *C07C 7/005* (2013.01); *C07C 7/12* (2013.01); *C07C 7/14* (2013.01); *C07C 7/144* (2013.01); *C07C 15/08* (2013.01)

(56) References Cited

U.S. PATENT DOCUMENTS

| | | | |
|---|---|---|---|
| 6,376,733 | B1 | 4/2002 | Ferraro et al. |
| 8,569,559 | B2 | 10/2013 | Ou |
| 9,975,820 | B2 | 5/2018 | Weiss et al. |
| 2002/0082462 | A1 | 6/2002 | Ferraro et al. |
| 2005/0167338 | A1 | 8/2005 | Miller et al. |
| 2017/0144106 | A1 | 5/2017 | McCool et al. |
| 2017/0362143 | A1 | 12/2017 | Bilaus et al. |

OTHER PUBLICATIONS

Silady, "UOP Isomar Process", Handbook of Petroleum Refining Processes, Chapter 2.5.

Commissaris, "UOP Parex Process", Handbook of Petroleum Refining Processes, Chapter 2.6.

International Search Report and Written Opinion dated May 6, 2020 pertaining to International application No. PCT/US2020/016466 filed Feb. 4, 2020, 14 pgs.

Zhang, C. et al. "Catalytic MFI zeolite membranes supported on $\alpha$-Al2O3 substrates for m-xylene isomerization" Journal of Membrane Science, vol. 389, Nov. 3, 2011, pp. 451-458.

Toch, K. et al. "A Single-Event MicroKinetic model for "ethylbenzene dealkylation/xylene isomerization" on Pt/H-ZSM-5 zeolite catalyst" Applied Catalysis A: General, vol. 425, Mar. 5, 2012, pp. 130-144.

Office Action pertaining to U.S. Appl. No. 16/282,408 dated Apr. 17, 2020, 29 pgs.

Notice of Allowance pertaining to U.S. Appl. No. 16/282,408 dated Jul. 22, 2020, 5 pgs.

METHODS AND SYSTEMS FOR PRODUCING PARA-XYLENE FROM C8-CONTAINING COMPOSITIONS

CROSS-REFERENCE TO RELATED APPLICATION

This application is a continuation application of U.S. patent application Ser. No. 16/282,408 filed Feb. 22, 2019, the entire disclosure of which is hereby incorporated herein by reference.

TECHNICAL FIELD

The present specification generally relates to methods and systems for producing and recovering para-xylene (p-xylene) from $C_8$-containing compositions.

BACKGROUND

Xylenes are important building blocks in the manufacture of plastics and synthetic fibers among other products, and demand for xylenes, in particular para-xylene, is increasing. Xylenes such as para-xylene can be obtained from $C_6$-$C_8$ aromatic streams produced in petrochemical processing operations. The $C_6$-$C_8$ aromatic stream can be processed to recover benzene, toluene, and the $C_8$ aromatics, which include para-xylene (p-xylene or PX), ortho-xylene (o-xylene or OX), meta-xylene (m-xylene or MX), and ethylbenzene (EB). However, because the boiling point temperatures of m-xylene, o-xylene, p-xylene, and ethylbenzene are very close, it is difficult to separate these $C_8$ aromatics by fractional distillation. Instead, the $C_8$ aromatics are commonly separated from one another by crystallization, which takes into account the differences in freezing points between the $C_8$ aromatics, or selective adsorption, in which zeolite materials are used to selectively adsorb one or more of the $C_8$ aromatics.

Some systems for producing p-xylene have combined the crystallization or selective adsorption operations with a xylene isomerization process to increase the yield of p-xylene. Xylene isomerization is commonly conducted in a fixed bed reactor by contacting the $C_8$ aromatics with an isomerization catalyst, such as a zeolite-based catalyst, at temperatures in excess of 350 degrees Celsius (° C.). These fixed bed xylene isomerization systems occupy a large footprint and require substantial amounts of energy to maintain the reaction temperature in the desired range. Further, returning the effluent from the xylene isomerization process back to the crystallization or selective adsorption process can greatly increase the volume of materials processed by the crystallization or selective adsorption process, which can greatly increase the size and energy consumption of these separation processes.

SUMMARY

Accordingly, ongoing needs exist for improved methods and systems for processing $C_8$-containing streams to produce p-xylene to further increase the yield and efficiency of p-xylene production. The processes and systems of the present disclosure may incorporate advanced membrane technology into the p-xylene production process which may improve the yield of p-xylene and reduce the size of the p-xylene recovery equipment (crystallizers or selective adsorption columns) needed to recover the p-xylene. The systems and methods for producing p-xylene of the present disclosure can include a xylene rerun column and a xylene processing loop, which may include a p-xylene recovery unit, a membrane isomerization unit, an ethylbenzene dealkylation unit, a membrane separation unit, and a stripper. The membrane isomerization unit may include a catalytic membrane, such as an acidic sulfonated polymeric membrane, for carrying out an isomerization process to convert m-xylene, o-xylene, ethylbenzene, or combinations of these into p-xylene. The membrane separation unit may include a carbon based membrane that is at least partially selective for p-xylene over m-xylene, o-xylene, and ethylbenzene, and is operable to produce a permeate that is rich in p-xylene and a retentate that is lean in p-xylene. The ethylbenzene dealkylation unit in combination with the stripper may operate to convert ethylbenzene to $C_{7-}$ compounds, such as toluene and benzene, and remove the $C_{7-}$ compounds from the p-xylene processing loop.

The methods of the present disclosure may include producing a xylene-containing stream from a $C_8$ aromatic containing stream and passing the xylene-containing stream to the xylene processing loop. In the xylene processing loop, at least a portion of the MX, OX, EB, or combinations of these are isomerized to PX, at least a portion of the EB is converted to one or more $C_{7-}$ compounds, $C_{7-}$ compounds may be removed from the xylene processing loop, the PX may be at least partially separated from the MX, OX, and EB in a membrane separation step, the PX may be recovered from the xylene processing loop by the PX recovery unit. Streams containing the MX, OX, and EB may be recycled back through various portions of the xylene recovery loop to further increase the yield of PX.

By incorporating a membrane isomerization process into the xylene processing loop and combining this with a membrane separation step to create a PX-rich permeate upstream of the PX recovery unit, the systems and methods of the present disclosure may increase the yield of PX and reduce the energy costs of PX recovery by reducing the size and energy requirements of the PX recovery system and reducing the energy required for isomerization of the $C_8$ aromatics to PX. Thus, the systems and methods of the present disclosure may reduce the capital costs and energy consumption for a given PX production rate by reducing the equipment sizes necessary to produce the given PX production rate.

According to one or more aspects of the present disclosure, a method for producing para-xylene (PX) may include separating a $C_8$ aromatic-containing composition into a xylene-containing effluent and a heavy effluent, the xylene-containing effluent comprising p-xylene (PX), ethylbenzene (EB), and one or both of m-xylene (MX) and o-xylene (OX). The method may further include isomerizing at least a portion of the MX, the OX, or both from the xylene-containing effluent to PX by contacting the portion of the MX, OX, or both with a catalytic membrane in a membrane isomerization unit. The method may further include dealkylating at least a portion of the EB in the xylene-containing composition to form one or more $C_{7-}$ compounds, subjecting at least a portion of the xylene-containing composition to a membrane separation unit to produce a permeate that is PX-rich and a retentate that is PX-lean, and recovering PX from the xylene-containing composition, the permeate, or both in a PX recovery unit to produce a PX product.

According to one or more other aspects of the present disclosure, a method for producing p-xylene from a $C_8$-aromatic-containing composition may include introducing a $C_8$ aromatic-containing composition to a xylene rerun column operable to separate the $C_8$ aromatic-containing composition into a xylene-containing effluent and a heavy effluent, the xylene-containing effluent comprising p-xylene (PX) and at least one of m-xylene (MX), o-xylene (OX), ethylbenzene (EB), or combinations of these. The method may further include passing the xylene-containing effluent to a PX processing loop. The PX processing loop may include a PX recovery unit operable to separate at least a PX product stream from at least a portion of the xylene-containing effluent, a membrane isomerization unit operable to convert at least a portion of the MX, OX, or both from the xylene-containing effluent to PX, an EB dealkylation unit operable to dealkylate EB from the xylene-containing effluent to produce benzene, toluene, other $C_7$-compounds, or combinations of these, and a membrane separation unit operable to produce a permeate that is PX-rich and a retentate that is PX-lean. The method may further include passing the PX product stream out of PX processing loop.

According to one or more other aspects of the present disclosure, a system for producing para-xylene (PX) from a $C_8$ aromatic-containing composition may include a xylene rerun column operable to separate the $C_8$ aromatic-containing composition into a xylene-containing effluent and a heavy effluent, the xylene-containing effluent comprising at least PX and one or more of ortho-xylene (OX), meta-xylene (MX), ethylbenzene (EB), or combinations of these. The system may further include a xylene processing loop that includes a PX recovery unit operable to separate the xylene-containing effluent into at least a PX product and a PX-depleted effluent, a membrane isomerization unit operable to convert at least a portion of the MX, OX, EB, or combinations of these from the xylene-containing effluent to PX, an ethylbenzene dealkylation unit operable to dealkylate at least a portion of the EB from the xylene-containing effluent to produce one or more $C_{7-}$ compounds, and a membrane separation unit operable to separate at least a portion of the xylene-containing stream into a permeate that is PX-rich and a retentate that is PX-lean.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, in which like structure is indicated with like reference numerals and in which.

Figure 1:
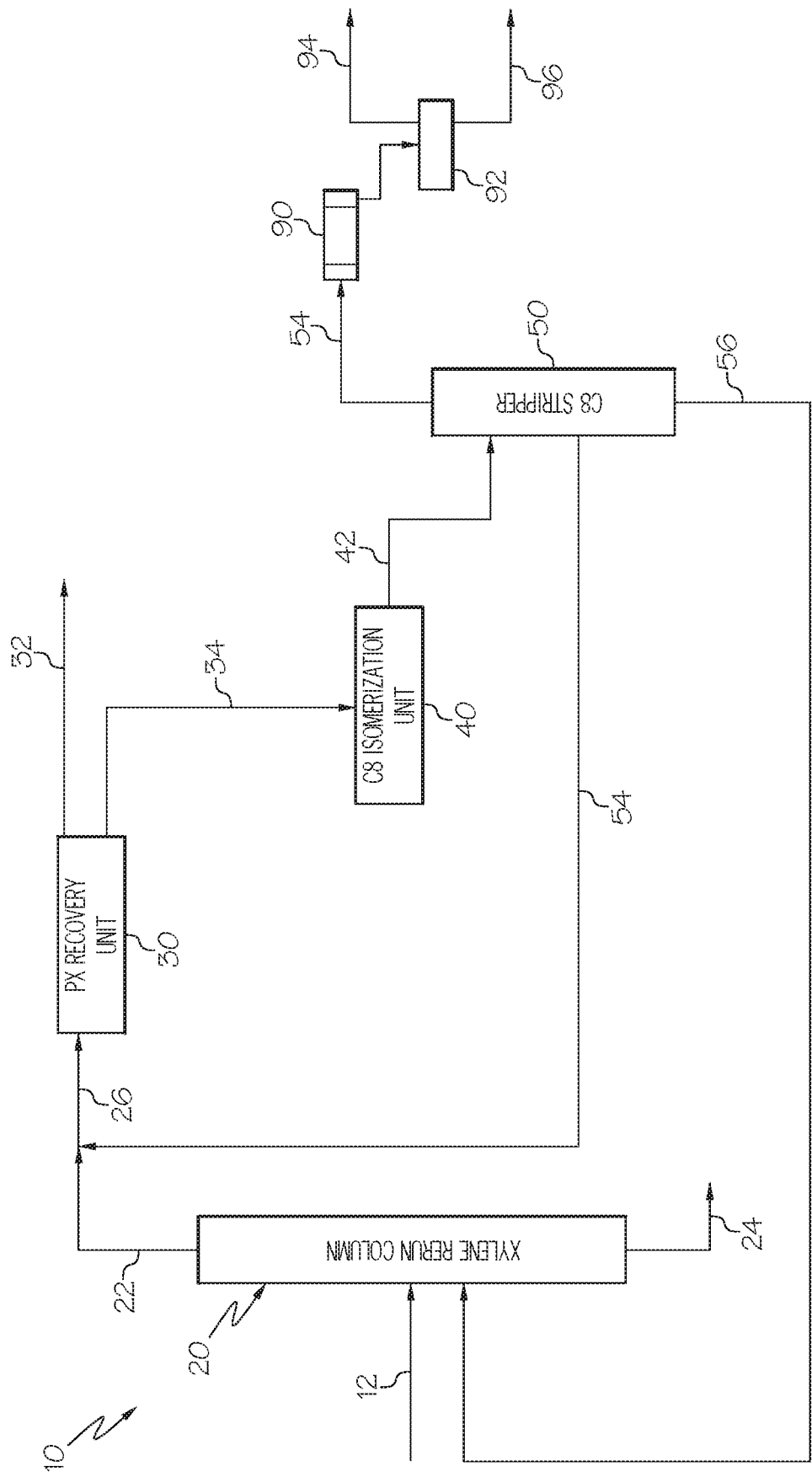
FIG. 1 schematically depicts a process flow diagram for a prior art system for producing p-xylene from a $C_8$-containing stream.

For the purpose of describing the simplified schematic illustrations and descriptions of FIGS. 1-6, the numerous valves, temperature sensors, flow meters, pressure regulators, electronic controllers, pumps, and the like that may be employed and well known to those of ordinary skill in the art of certain chemical processing operations are not included. Further, accompanying components that are often included in typical chemical processing operations, such as valves, pipes, pumps, agitators, heat exchangers, instrumentation, internal vessel structures, or other subsystems may not be depicted. Though not depicted, it should be understood that these components are within the spirit and scope of the present embodiments disclosed. However, operational components, such as those described in the present disclosure, may be added to the embodiments described in this disclosure.

Arrows in the drawings refer to process streams. However, the arrows may equivalently refer to transfer lines which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows which do not connect two or more system components may signify a product stream which exits the depicted system or a system inlet stream which enters the depicted system. Product streams may be further processed in accompanying chemical processing systems or may be commercialized as end products.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagrams of FIGS. 1-6. Mixing or combining may also include mixing by directly introducing both streams into a like system component, such as a fractionation column, membrane separation unit, reactor, stripper, crystallizer, absorption column, or other system component. For example, it should be understood that when two streams are depicted as being combined directly prior to entering a system component, the streams could equivalently be introduced into the system component separately and be mixed in the system component.

Reference will now be made in greater detail to various embodiments, some embodiments of which are illustrated in the accompanying drawings. Whenever possible, the same

DETAILED DESCRIPTION

Figure 2:
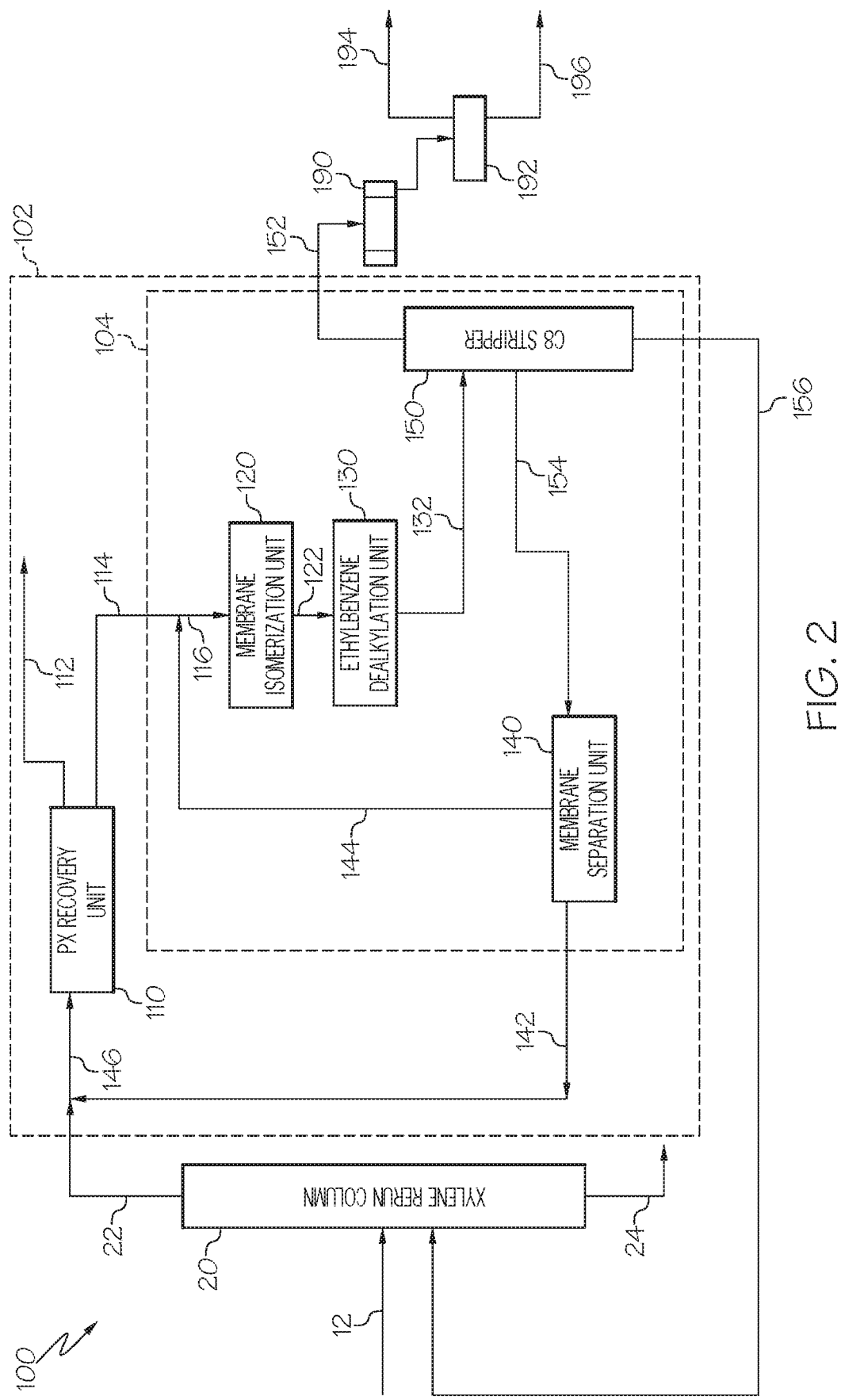
FIG. 2 schematically depicts a process flow diagram for a system for producing p-xylene from a $C_8$-containing stream, according to one or more embodiments described in this disclosure.

Embodiments of the present disclosure are directed to methods and system for producing p-xylene (PX) from $C_8$-containing compositions. The systems and methods disclosed herein may include membrane technology in isomerization of xylenes top-xylene and in separation of a xylenes containing stream into a permeate having a greater concentration of p-xylene and a retentate having a lesser concentration of p-xylene. Referring to FIG. 2, an embodiment of system 100 according to the present disclosure is depicted and includes a xylene rerun column 20 and a xylene processing loop 102. The xylene processing loop 102 may include a p-xylene recovery unit 110, a membrane isomerization unit 120 for isomerizing at least m-xylene and o-xylene to p-xylene. The xylene processing loop 102 may further include an ethylbenzene dealkylation unit 30 for dealkylating ethylbenzene to $C_{7-}$ compounds, a stripper 150 operable to remove the $C_{7-}$ compounds from the xylene processing loop 102, and a membrane separation unit 140 for separating a stream in the xylene processing loop 102 into the permeate 142 and the retentate 144. The permeate 142 may be returned to the p-xylene recovery unit 110 for recovery of p-xylene from the permeate 142 and the retentate 144 may be recirculated back through a xylene isomerization loop 104 for further conversion of m-xylene, o-xylene, and ethylbenzene. The systems and methods of the present disclosure may increase the yield of p-xylene and may reduce the size and energy consumption of the p-xylene recovery unit 110 by reducing the volume materials passed to the p-xylene recovery unit 110.

As used in this disclosure, the term "$C_8$-containing composition" may refer to a composition or stream that contains one or more of the $C_8$ aromatic compounds m-xylene, o-xylene, p-xylene, and ethylbenzene.

As used in this disclosure, the term "xylenes," when used without a designation of the isomer, such as the prefix para, meta, or ortho, may refer to one or more of meta-xylene, ortho-xylene, para-xylene, and mixtures of these xylene isomers. For convenience throughout this disclosure, meta-xylene, ortho-xylene, and para-xylene, may be referred to in this disclosure using the acronyms MX, OX, and PX, respectively, or alternatively by the names m-xylene, o-xylene, or p-xylene, respectively. Ethylbenzene may be referred to in this disclosure using the acronym EB.

As used in this disclosure, the term "fractionation" may refer to a process of separating one or more constituents of a composition in which the constituents are divided from each other during a phase change based on differences in properties of each of the constituents. As an example, as used in this disclosure, "distillation" refers to separation of constituents of a liquid composition based on differences in the boiling point temperatures of constituents of a liquid composition.

As used in this disclosure, the terms "upstream" and "downstream" refer to the relative positioning of unit operations with respect to the direction of flow of the process streams. A first unit operation of a system is considered "upstream" of a second unit operation if process streams flowing through the system encounter the first unit operation before encountering the second unit operation. Likewise, a second unit operation is considered "downstream" of the first unit operation if the process streams flowing through the system encounter the first unit operation before encountering the second unit operation. For the xylene processing loops and xylene isomerization loops described in the present disclosure, "upstream" and "downstream" are relative to a first unit, which is the unit operation encountered by the xylene-containing stream passed out of the xylene rerun column 20 (such as the PX-recovery unit 110 in FIGS. 2-4 and membrane separation unit 140 in FIGS. 5 and 6). For example, in FIG. 1, the PX-recovery unit 110 is the first unit, and the membrane separation unit 140 is considered to be "downstream" of the PX-recovery unit 110, even though a stream is passed from the membrane separation unit 140 to the PX-recovery unit 110.

In this disclosure, a stream or effluent that is passed "directly" from one unit to another unit refers to passing the effluent from the first unit to the second unit without passing the effluent through an intervening unit operation that removes or reacts one or more constituents of the effluent. Passing an effluent "directly" from one unit to another unit does not exclude passing the effluent through a heat exchanger, static mixer, valve, or other ancillary equipment. Passing the effluent "directly" from a first unit to a second unit also does not exclude combining the effluent with a supplemental stream to form a combined stream before introducing the combined stream to the second unit. Passing an effluent "directly" from a first unit to a second unit is intended to exclude passing the effluent to an intervening separator or reactor that substantially changes the chemical nature of the effluent before it gets to the second unit.

PX may be present in $C_8$-aromatic-containing compositions produced in petrochemical processes. The PX is generally present in a mixture of $C_8$ aromatic compounds, which may include the other xylene isomers, MX and OX, as well as EB. The challenge in producing PX is separating the PX from the MX, OX, EB, or combinations of these due to the similarities in the boiling point temperatures of these compounds. Processes for recovering PX from $C_8$-containing compositions include separation of PX from the other $C_8$ aromatics using crystallization based on differences in freezing point temperatures or selective adsorption, in which a zeolite selectively adsorbs PX over the other $C_8$ aromatic compounds.

Referring now to FIG. 1, a conventional PX system 10 for producing PX according to the prior art is depicted. The conventional PX system 10 includes a xylene rerun column 20 for separating a $C_8$-containing composition 12, which includes the $C_8$ aromatics, into a xylene-containing effluent 22 and a heavy stream 24. The xylene-containing effluent 22 is then passed to a PX recovery unit 30, which is operable to separate the xylene-containing effluent 22 into a PX stream 32 and a PX-lean stream 34. To improve the yield of PX, the PX-lean stream 34 may be passed to a $C_8$ isomerization unit 40 that may be operable to isomerize at least a portion of the MX, OX, EB, or combinations of these compounds to PX to produce a $C_8$ isomerization effluent 42. The $C_8$ isomerization effluent 42 may be passed to a stripper to remove $C_{7-}$ compounds and other compounds having boiling temperatures less than the boiling temperatures of the $C_8$ aromatic compounds in a light stream 54. The light stream 54 may be further processed in a condenser 90 and supplemental separator 92 to produce a light hydrocarbon gas stream 94 and a light aromatic stream 96. Constituents having a boiling temperature greater than the $C_8$ aromatic compounds may be passed back to the xylene rerun column 20 in a bottoms stream 56. The remaining stream 52 containing the $C_8$ aromatics is recycled back to the PX recovery unit 30.

Including the $C_8$ isomerization unit 40 in the conventional PX system 10 may improve the yield of PX by converting at least a portion of the MX, OX, EB, or combinations of these compounds to PX. However, incorporation of the $C_8$ isomerization unit 40 in the conventional PX system 10 may increase the size of the PX-recovery unit 30, which represents a substantial portion of the energy consumption of the conventional PX system 10. As shown in FIG. 1, the PX from the $C_8$ isomerization unit 40 along with the remaining OX, MX, EB are all passed back to the PX-recovery unit 30 and must be accounted for in sizing the PX-recovery unit 30. In other words, the PX-recovery unit 30 in the conventional PX system 10 must be sized to accommodate the additional throughput needed to accommodate the recycle of all of the OX, MX, EB, and PX from the $C_8$ isomerization unit 40. For a PX system 10 in which the PC-recovery unit 30 is a UOP PAREX™ process and the $C_8$ isomerization unit 40 is a UOP ISOMAR™ process, the PX-recovery unit 30 may represent more than 60% of the total electric power consumption and about 80% of the fuel oil consumption of the PX system 10. Any reduction in the size of the PX-recovery unit 30 can have a substantial impact on the energy consumption of the PX system 10. Additionally, the size of the PX-recovery unit 30 may represent a substantial portion of the capital cost of the conventional PX system 10.

Referring again to FIG. 2, a system for producing PX from a $C_8$-aromatic-containing composition 12 according to the present disclosure is depicted, the system generally referred to by reference number 100. The system 100 includes the xylene rerun column 20 and a xylene processing loop 102 that includes a PX-recovery unit 110, a membrane isomerization unit 120, an EB dealkylation unit 130, and a membrane separation unit 140. The xylene processing loop 102 may also include the stripper 150. The PX-recovery unit 110 is operable to separate a PX product 112 from the other constituents of the xylene-containing stream. The EB dealkylation unit 130 may increase the yield of PX by converting at least a portion of the MX, OX, EB, or combinations of these to PX.

The EB dealkylation unit 130, the membrane separation unit 140, and the stripper 150 may cooperate to reduce the volume of constituents recycled back through the PX-recovery unit 110, which may reduce the size of the PX-recovery unit 110. For example, the EB dealkylation unit 130 may convert EB to one or more $C_{7-}$ compounds, which may then be removed from the xylene processing loop 102 by the stripper 150. Conversion of EB to $C_{7-}$ compounds and removal of the $C_{7-}$ compounds from the xylene processing loop 102 may prevent build-up of these constituents in the xylene processing loop 102, which may reduce the volume of constituents recycled back through the PX-recovery unit 110. Additionally, the membrane separation unit 140 may be operable to separate the constituents in the xylene processing loop 102 into a permeate 142 and a retentate 144. The permeate 142 may be PX-rich, meaning that the permeate 142 has a greater concentration of PX than the retentate 244. The permeate 142 may be passed to the PX-recovery unit 110 for further recovery of PX. The retentate 144 may be PX-lean, meaning that the retentate 144 may have a lesser concentration of PX compared to the permeate 142. The majority of the retentate 144 may be OX, MX, EB, or combinations of these, and the retentate 144 may be recycled back into the xylene processing loop 102 downstream of the PX-recovery unit 110 and is not passed through the PX-recovery unit 110. Thus, the membrane separation unit 140 may enable the MX, OX, EB, or combinations of these to continue to pass through the membrane isomerization unit 120 and EB dealkylation unit 130 without passing through the PX-recovery unit 110. This may additionally reduce the volume of compounds passed through the PX-recovery unit 110, which may reduce the required size of the PX-recovery unit 110 for producing a given production rate of PX. Incorporation of the EB dealkylation unit 130 and membrane separation unit 140 into the system 100, therefore, reduces the volume of constituents passed to the PX-recovery unit 110 to reduce the required size of the PX-recovery unit 110. Each of the separate unit operations of system 110 will now be described in further detail.

The $C_8$-aromatic-containing composition 12 may be any stream that includes one or more $C_8$ aromatic compounds, such as MX, OX, PX, EB, or combinations of these. In addition to the $C_8$ aromatic compounds, the $C_8$-aromatic-containing composition 12 may include other constituents, such as hydrocarbons having less than 8 carbon atoms or greater than 8 carbon atoms. For example, the $C_8$-aromatic-containing composition 12 may include toluene, benzene, $C_{9+}$ aromatic compounds, or combinations of these. The other constituents of the $C_8$-aromatic-containing composition 12 may include alkanes, alkenes, aromatics, cyclic hydrocarbons, other types of hydrocarbons, or combinations of hydrocarbons. In some embodiments, the $C_8$-containing composition may include one or more $C_6$-$C_8$ hydrocarbon streams from a petrochemical processing operation.

Referring to FIG. 2, the $C_8$-aromatic-containing composition 12 is passed to the xylene rerun column 20, which is operable to separate the $C_8$-aromatic-containing composition 12 into at least a xylene-containing effluent 22 and a heavy effluent 24. The xylene rerun column 20 may be any separator capable of separating the xylene-containing effluent 22 from the $C_8$-aromatic-containing composition 12. In some embodiments, the xylene rerun column 20 may be a fractional distillation column operable to separate the $C_8$-aromatic-containing composition 12 into at least a xylene-containing effluent 22 and a heavy effluent 24. In some embodiments, the xylene rerun column 20 may further be operable to produce an optional lesser boiling point stream that includes constituents of the $C_8$-aromatic-containing composition 12 having boiling point temperatures less than the $C_8$ aromatics in the $C_8$-aromatic-containing composition 12. In some embodiments, the xylene rerun column 20 may include a plurality of distillation columns to separate the $C_8$-aromatic-containing composition 12 into the xylene-containing effluent 22, the heavy effluent 24, and an optional lesser boiling point stream (not shown). The optional lesser boiling point stream may include constituents of the $C_8$-aromatic-containing composition having a boiling point temperature greater than the $C_8$ aromatics.

The xylene-containing effluent 22 may include one or more of MX, OX, PX, EB, or combinations of these. In some embodiments, the xylene-containing effluent 22 may include MX, OX, PX, and EB. The xylene-containing effluent 22 may also include toluene, benzene, $C_{9+}$ aromatic compounds, other hydrocarbon compounds, or combinations of these. The xylene-containing effluent 22 may be passed out of the xylene rerun column 20 to the xylene processing loop 102. The heavy stream 24 may include constituents of the $C_8$-aromatic-containing composition 12 having boiling point temperatures greater than the boiling temperatures of the MX, OX, PX, or EB. For example, the heavy stream 24 may include $C_9$ aromatic compounds having boiling temperatures greater than the $C_8$ aromatics. The heavy stream 24 may be passed out of the xylene rerun column 20, which may pass the heavy stream 24 out of the system 100. In some embodiments, the xylene rerun column 20 may optionally separate out lesser boiling point constituents of the $C_8$-aromatic-containing composition 12. The lesser boiling point constituents may have boiling point temperatures less than the $C_8$ aromatics. The lesser boiling point constituents of the $C_8$-aromatic-containing composition 12 may include compounds such as toluene, benzene, and other components having boiling point temperatures less than the $C_8$ aromatics. The lesser boiling point constituents may be passed out of the xylene rerun column 20 in the optional lesser boiling point stream (not shown).

Referring to FIG. 2, the xylene-containing effluent 22 is passed to the xylene processing loop 102, which, as previously described in this disclosure, includes the PX-recovery unit 110, the membrane isomerization unit 120, the EB dealkylation unit 130, the membrane separation unit 140, and the stripper 150. The PX-recovery unit 110 may be operable to separate at least a portion of the xylene-containing effluent 22 into a PX product 112 and a PX-depleted effluent 114. The feed stream to the PX-recovery unit 110 may include the xylene-containing effluent 22, a permeate stream 142 from the membrane separation unit 140, or combinations of these. The PX-recovery unit 110 may be a crystallization process, a selective adsorption process, other process capable of selectively separating PX from MX, OX, and EB, or combinations of PX separation processes. In some embodiments, the PX-recovery unit 110 may include a fractional crystallization process that separations PX from the other $C_8$ aromatics based on the difference in freezing point temperature of PX relative to the other $C_8$ aromatics. In other embodiments, the PX-recovery unit 110 may include a selective adsorption process in which the xylene-containing effluent 22 is contacted with molecular sieve, such as a zeolite material, to selectively adsorb the PX relative to the other $C_8$ aromatics. After removing the MX, OX, EB, or combinations of these from the zeolite material, the PX may be desorbed from the zeolite to recover the PX.

The PX recovery unit 110 may have a size that is less than a size of PX recovery unit 30 in the conventional PX system of FIG. 1. As used in the present disclosure, the "size factor" of the PX recovery unit 110 may be defined as the inlet volume flow rate to the PX recovery unit 110 divided by the inlet volume flow rate of PX recovery unit 30 for the conventional PX system 10 of FIG. 1. The PX recovery unit 110 may have a size factor of less than or equal to 0.70, less than or equal to 0.60, less than or equal to 0.50, or even less than or equal to 0.45. In some embodiments, the PX recovery unit 110 may have a size factor of from 0.20 to 0.70, from 0.20 to 0.60, from 0.20 to 0.50, from 0.20 to 0.45, from 0.25 to 0.70, from 0.25 to 0.60, from 0.25 to 0.50, or from 0.25 to 0.45. The size factor of the PX recovery unit 110 may be influenced by the feed composition, the efficiency of the membrane separation unit 140, or other factors.

The PX product 112 may be passed out of the PX-recovery unit 110. The PX product 112 may have a concentration of PX of greater than or equal to 99.0 wt. %, such as greater than or equal to 99.5 wt. %, or even greater than or equal to 99.8 wt. % based on the total weight of the PX product 112. The PX product 112 may also include very small concentrations of MX, OX, EB, or combinations of these, such as less than 1 wt. %, less than 0.5 wt. %, less than 0.2 wt. %, or even less than 0.1 wt. % MX, OX, EB, or combinations of these based on the total weight of the PX product 112. Passing the PX product 112 out of the PX-recovery unit 110 may pass the PX product 112 out of the system 100. The PX product 112 may be collected as a product or transported to one or more other operations as an intermediate to produce additional petrochemical products.

Figure 3:
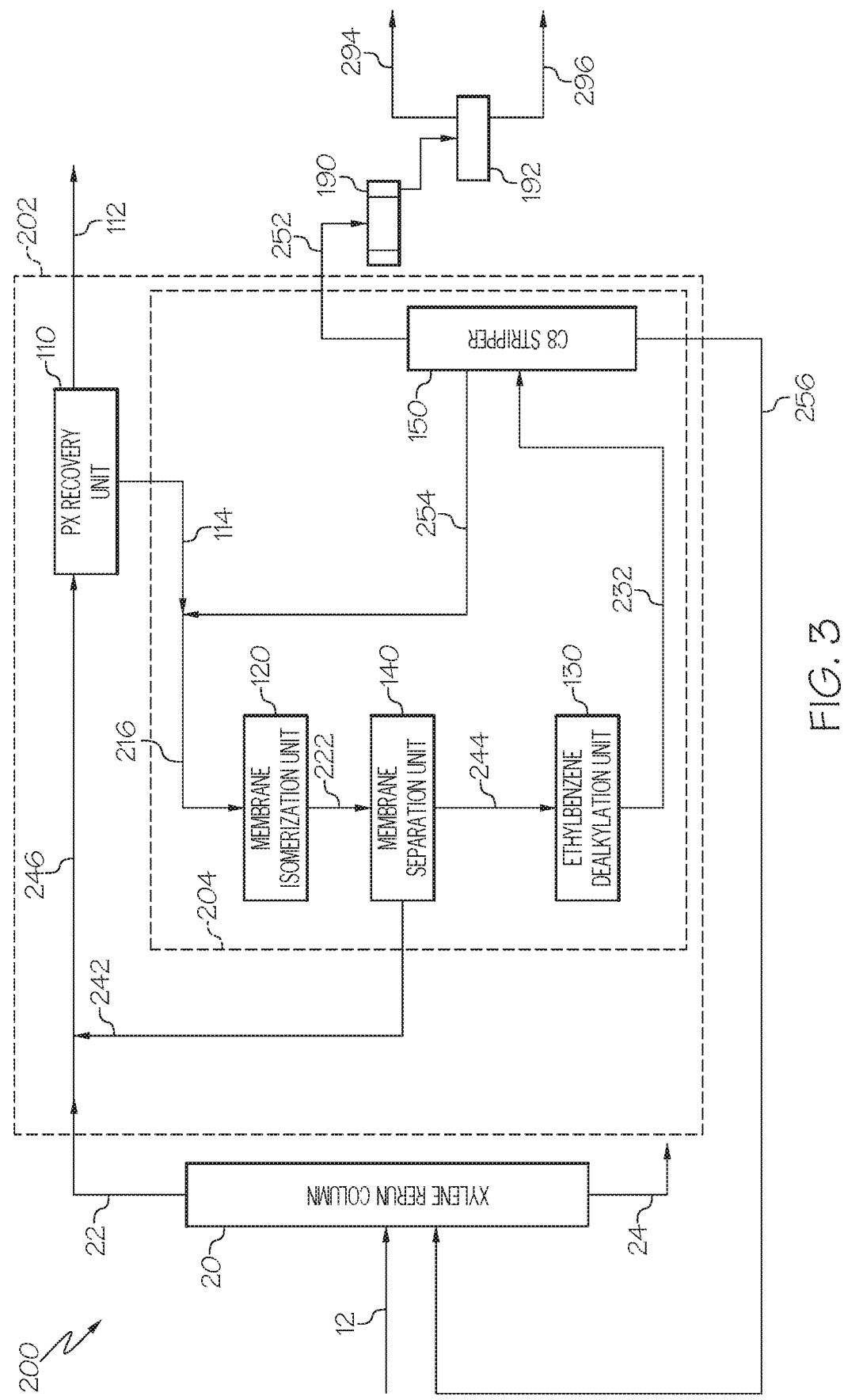
FIG. 3 schematically depicts a process flow diagram for another embodiment of a system for producing p-xylene from a $C_8$-containing stream, according to one or more embodiments described in this disclosure.

The filtrate from the crystallization process, the raffinate from the selective adsorption process, or both may be passed out of the PX-recovery unit 110 as the PX-depleted effluent 114. The PX-depleted effluent 114 may have a concentration of PX less than the concentration of PX in the xylene-containing effluent 22. The PX-depleted effluent 114 may include the MX, OX, EB, or combinations of these from the xylene-containing effluent 22, as well as the PX not separated in the PX-recovery unit 110. The PX-depleted effluent 114 may include other constituents of the xylene-containing effluent 22 that pass through the PX-recovery unit 110, The PX-depleted effluent 114 may be passed out of the PX-recovery unit 110 to one or more downstream operations in the xylene processing loop 102. In some embodiments, the PX-depleted effluent 114 may be passed from the PX-recovery unit 110 to the membrane isomerization unit 120, as shown in FIGS. 2, 3, and 5. In other embodiments, the PX-depleted effluent 114 may be passed to the EB dealkylation unit 130, which will be described subsequently in this disclosure in relation to FIGS. 4 and 6.

Referring again to FIG. 2, the membrane isomerization unit 120 may be operable to isomerize at least a portion of the MX, OX, or both from the xylene-containing effluent 22 to PX to produce an isomerate 122. The membrane isomerization unit 120 may increase the yield of PX obtained from the xylene-containing effluent 22 and increase the concentration of PX in the isomerate 122 by converting at least a portion of the MX, OX, or both from the xylene-containing effluent 22 to PX. The membrane isomerization unit 120 may be operable to contact the MX, OX, or both from the xylene-containing effluent 22 with an isomerization catalyst under temperature and pressure conditions sufficient to isomerize at least a portion of the MX, OX, or both to PX. In some embodiments, the membrane isomerization unit 120 may also optionally convert at least a portion of EB from the xylene-containing effluent 22 to MX, OX, PX, or combinations of these.

The membrane isomerization unit 120 may include a reactor that includes a catalytic membrane and may be operable to contact the MX, OX, and optionally EB with the catalytic membrane to facilitate isomerization of at least a portion of the MX, OX, or optional EB to PX. In some embodiments, the membrane isomerization unit 120 may be a catalytic membrane reactor configured to conduct a pervaporation process over a catalytic membrane to isomerize at least a portion of the MX, OX, and optionally EB, to PX. The pervaporation process of the membrane isomerization unit 120 may include contacting the portion of the xylene-containing effluent 22 with a first side of the catalytic membrane and withdrawing a vapor permeate from a second side of the catalytic membrane opposite the first side. The catalytic membrane in the membrane isomerization unit 120 may be an ionomer, such as sulfonated polymers, sulfonated copolymers, or combinations of these that have been found to be useful as acidic membranes for xylene isomerization. In some embodiments, the catalytic membrane may be an acidic sulfonated polymeric membrane. In some embodiments, the catalytic membrane may be a NAFION™ polymer membrane, such as a NAFION™-H polymer membrane manufactured by the Chemours Company. NAFION™-H polymer is a copolymer of a tetrafluoroethylene and perfluorinated sulfonated vinyl ether. Perfluorinated polymers have C—F bonds which provide chemical and thermal stability to the polymer membrane to assist in maintaining the integrity of the membrane. The sulfonic acid groups coupled to the perfluorinated backbone provides very high acidity to the polymer. Other acidic sulfonated polymer membrane materials may also be suitable as the catalytic membrane in the membrane isomerization unit 120.

The isomerization reaction may take place as the MX, OX, and EB contact the catalytic isomerization membrane and the product is drawn through the catalytic membrane. The vapor permeate recovered from the permeate side of the catalytic membrane may be cooled and condensed, the cooling reducing the vapor pressure on the permeate side of the membrane to provide a driving force for the pervaporation process.

In some embodiments, the permeate side of the catalytic membrane may be maintained at a pressure less than the feed side of the membrane. In some embodiments, the permeate side of the catalytic membrane may be subjected to a partial vacuum (pressure less than atmospheric pressure, for example 1 atmosphere=101.3 kilopascals (kPa) at sea level). For example, in some embodiments, the pressure on the permeate side of the catalytic membrane may be maintained at a pressure of less than 1 atmosphere.

The pervaporation process of the membrane isomerization unit 120 using an acidic sulfonated polymer membrane as the catalytic membrane may enable isomerization of MX, OX, and optionally EB to PX at lesser temperatures compared to conventional xylene isomerization processes, such as fixed bed isomerization reactors using inorganic catalysts. The reduced operating temperature of the membrane isomerization unit 120 may reduce the energy consumption of the membrane isomerization unit 120 compared to conventional xylene isomerization processes. The membrane isomerization unit 120 may be operated at a temperature sufficient to isomerize at least a portion of the MX, OX, or EB to PX when the MX, OX, or EB is contacted with the catalytic membrane. In some embodiments, a reaction zone of the membrane isomerization unit 120 may be operated at an isomerization reaction temperature of from 20° C. to 350° C., such as from 20° C. to 300° C., from 20° C. to 275° C., from 20° to 250° C., from 20° C. to 225° C., from 20° C. to 200° C., from 30° C. to 350° C., from 30° C. to 300° C., from 30° C. to 275° C., from 30° to 250° C., from 30° C. to 225° C., from 30° C. to 200° C., from 50° C. to 350° C., from 50° C. to 300° C., from 50° C. to 275° C., from 50° to 250° C., from 50° C. to 225° C., or from 50° C. to 200° C.

In some embodiments, the membrane isomerization unit 120 may be a fixed bed catalytic reactor that includes an inorganic catalytic membrane, such as a zeolite catalytic membrane, such as a mordenite framework zeolite, for isomerization of MX, OX, or both to PX. The isomerization reaction in a fixed bed reactor using an inorganic zeolite based catalytic membrane may required increased reaction temperatures, such as reaction temperatures of from 300° C. to 450° C. Fixed bed reactors utilizing zeolite catalyst membranes may also have a substantially larger equipment footprint compared to the pervaporation process previously described for the membrane isomerization unit 120.

The isomerate 122 may have a greater concentration of PX than the total concentration of PX in the feed to the membrane isomerization unit 120. In FIG. 2, the feed to the membrane isomerization unit 120 may be a combined isomerization feed 116, which may include the PX-depleted effluent 114 as well as the retentate 144. However, as will be discussed in further detail subsequently in this disclosure, the feed to the membrane isomerization unit 120 may include different streams based on the configuration of the xylene processing loop 102. Additionally, the isomerate 122 may have concentrations of MX and OX that are less than the concentrations of MX and OX in the streams passed to the membrane isomerization unit 120. In some embodiments, the isomerate 122 may have a concentration of EB less than the concentration of EB in the streams passed to the membrane isomerization unit 120. The isomerate 122 may also include benzene, toluene, $C_{9+}$ compounds, or combinations of these, which may be generated within the membrane isomerization unit 120 or passed through the membrane isomerization unit 120 as portions of the streams introduced to the membrane isomerization unit 120.

Referring again to FIG. 2, the EB dealkylation unit 130 may be operable to dealklylate EB in the xylene processing loop 102 to $C_{7-}$ compounds, such as toluene and benzene. The $C_{7-}$ compounds may be hydrocarbons having less than or equal to 7 carbon atoms, such as 1, 2, 3, 4, 5, 6, or 7 carbon atoms. The $C_{7-}$ compounds may include toluene, benzene, methane, ethane, other hydrocarbons having less than or equal to 7 carbon atoms, and combinations of these. The EB dealkylation unit 130 may include a reactor and a dealkylation catalyst disposed within the reactor. The EB dealkylation unit 130 may be operable to contact EB with the dealkylation catalyst under conditions sufficient to convert the EB to the $C_{7-}$ compounds to produce a dealkylation effluent 132. In some embodiments, the EB dealkylation unit 130 may be a fixed bed reactor that includes at least one dealkylation reaction zone in which the EB is contacted with the dealkylation catalyst.

The dealkylation catalyst may be a catalyst capable of catalyzing the dealkylation of EB, such as dealkylating EB to benzene and ethylene for example. In some embodiments, the dealkylation catalyst may be operable to promote transalkylation of EB to benzene and diethylbenzene. In some embodiments, the dealkylation catalysts may be a zeolite based catalyst, such as a ZSM-5 zeolite catalyst. The dealkylation catalyst may be a medium pore size zeolite, such as a mesoporous zeolite. The dealkylation catalyst may include one or a combination of metals having dehydrogenation functionality, such as, but not limited to metals in Groups 6-10, 14, and 15 of the International Union of Pure and Applied Chemistry (IUPAC) periodic table. The dealkylation catalyst may include one or a combination of manganese (Mn), molybdenum (Mo), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), tin (Sn), lead (Pb), antimony (Sb), or bismuth (Bi). In some embodiments, the dealkylation catalyst may be a mesoporous ZSM-5 zeolite loaded with molybdenum. Other commercially available dealkylation catalysts may also be suitable for converting EB into benzene, toluene, or other $C_{7-}$ compounds. In some embodiments, the EB dealkylation may be catalyzed by a $C_8$ isomerization catalyst, such as the acidic sulfonated polymer membranes, zeolite membranes, and other $C_8$ isomerization catalyst membranes previously discussed herein.

The EB dealkylation unit 130 may be operated at conditions sufficient to convert at least a portion of the EB passed to the EB dealkylation unit 130 to one or more $C_{7-}$ compounds, such as benzene or toluene. The EB dealkylation unit 130 may be operated at a reaction temperature of from 200° C. to 550° C., from 250° C. to 400° C., or even from 300° C. to 350° C. The EB dealkylation unit 130 may be operated at a pressure of from 1 bar to 50 bar, from 10 bar to 40 bar, or even from 20 bar to 30 bar, and a weight hourly space velocity (WHSV) of from 0.1 per hour ($hr^{-1}$) and 100 $hr^{-1}$, from 1 $hr^{-1}$ to 50 $hr^{-1}$, or even from 1 $hr^{-1}$ to 10 $hr^{-1}$. The EB dealkylation unit 130 may also cause dealkylation of xylenes passed to the EB dealkylation unit 130. In some embodiments, the dealkylation catalyst and reaction conditions in the EB dealkylation unit 130 may be modified to minimize the dealkylation of xylenes within the EB dealkylation unit 130.

The dealkylation effluent 132 may be passed out of the EB dealkylation unit 130. The dealkylation effluent 132 may have a concentration of EB less than a concentration of EB in the streams passed to the EB dealkylation unit 130. For example, the feed to the EB dealkylation unit 130 may be the isomerate 122 passed from the membrane isomerization unit 120, and a concentration of EB in the dealkylation effluent 132 may be less than the concentration of EB in the isomerate 122. The dealkylation effluent 132 may include at least a portion of the MX, OX, and PX passed to the EB dealkylation unit 130 as well as the remaining EB that did not undergo dealkylation in the EB dealkylation unit 130. The dealkylation effluent 132 may also include the reaction products of the dealkylation reaction, which include the plurality of $C_{7-}$ compounds produced by dealkylation of the EB. These $C_{7-}$ compounds may include at least one or a combination of benzene, toluene, ethylene, or other $C_1$-$C_7$ hydrocarbons.

Referring again to FIG. 2, the dealkylation effluent 132 is passed from the EB dealkylation unit 130 to the stripper 150. In some embodiments, the dealkylation effluent 132 may be passed directly from the EB dealkylation unit 130 to the stripper 150. The stripper 150 may be operable to remove the $C_{7-}$ compounds, and optionally, compounds having a boiling temperature greater than the $C_8$ aromatics in the dealkylation effluent 132. In some embodiments, the stripper 150 may be a fractionation column operable to separate the dealkylation effluent 132 into a $C_{7-}$ effluent 152, an EB-depleted effluent 154, and a stripper bottoms 156. The $C_{7-}$ effluent 152 may include the $C_{7-}$ compounds, which have a boiling temperature less than the boiling point temperature of the $C_8$ aromatics (xylenes and EB). The $C_{7-}$ effluent 152 may be passed to one or more downstream operations, such as a condenser 190 and a supplemental separator 192 downstream of the condenser 190. The supplemental separator 192 may be operable to separate the $C_{7-}$ effluent 152 into one or more streams, such as a light gas stream 194 and a light aromatic stream 196, which may include the benzene and toluene from the EB dealkylation reaction. The stripper bottoms 156 may include compounds having a boiling point temperature greater than the boiling point temperature range of the $C_8$ aromatics. For example, in some embodiments, the stripper bottoms 156 may include $C_9$ aromatic compounds or other compounds having boiling point temperatures greater than the $C_8$ aromatics. The stripper bottoms 156 may be passed from the stripper 150 back to the xylene rerun column 20, in which any $C_8$ aromatics from the stripper bottoms 156 can be recovered and returned to the xylene processing loop 102 through the xylene-containing effluent 22.

The EB-depleted effluent 154 may include the $C_8$ aromatics from the dealkylation effluent 132 and may be passed out of the stripper 150 to another operation in the xylene processing loop 102. For example, in FIG. 2, the EB-depleted effluent 154 may be passed from the stripper 150 to the membrane separation unit 140. In some embodiments, the EB-depleted effluent 154 may be substantially free of $C_{7-}$ compounds. As used in this disclosure, a composition that is "substantially free" of a constituent, such as a compound, substance, element, or other constituent, may refer to the composition having less than 1 wt. % of that constituent based on the total weight of the composition. In some embodiments, the EB-depleted effluent 154 may have less than 1 wt. % $C_{7-}$ compounds based on the total weight of the EB-depleted effluent 154.

The EB dealkylation unit 130 in combination with the stripper 150 may be operable to prevent the buildup of EB in the xylene processing loop 102 by converting the EB to $C_{7-}$ compounds in the EB dealkylation unit 130 and removing the $C_{7-}$ compounds from the xylene processing loop 102 in the stripper 150. Removal of EB and $C_{7-}$ compounds from the xylene processing loop 102 may reduce the quantity (volume) of materials passed through the PX-recovery unit 110, which may contribute to reducing the size and energy requirements of the PX-recovery unit 110.

The membrane separation unit 140 may be operable to separate a composition that includes PX and one or more than one of MX, OX, and EB into a permeate 142 and a retentate 144. The permeate 142 may be a PX-rich stream, meaning that the permeate 142 may have a greater concentration of PX compared to retentate 144. The permeate 142 may also include lesser concentrations of MX, OX, and EB compared to the retentate 144. The retentate 144 may be a PX-lean stream, meaning that the retentate 144 may have a lesser concentration of PX compared to the permeate 142. The retentate 144 may have greater concentrations of MX, OX, and EB compared to the permeate 142.

The membrane separation unit 140 may include a semipermeable membrane having greater selectivity for PX compared to the selectivity for each of MX, OX, and EB. In some embodiments, the membrane separation unit 140 may include a carbon-based membrane, such as carbon-based molecular sieve membranes. Carbon-based molecular sieve membranes may be produced by known methods, such as by cross-linking a polyvinylidene difluoride (PVDF) membrane and then subjecting the cross-linked PVDF membrane to pyrolysis. The carbon-based molecular sieve membrane of the membrane separation unit 140 may be in the form of a dense flat sheet, a porous flat sheet, or asymmetric hollow fibers. In some embodiments, the membrane separation unit 140 may include asymmetric carbon-based molecular sieve hollow fiber membranes. The carbon-based membrane of the membrane separation unit 140 may be different than the catalytic membrane in the membrane isomerization unit 120.

Referring again to FIG. 2, in some embodiments, a method for producing PX using the systems described in this disclosure, such as system 100, includes separating a $C_8$ aromatic-containing composition to produce a xylene-containing composition (xylene-containing effluent 22) and a heavy composition (heavy stream 24). The xylene-containing composition may include PX, EB, and one or both of MX and OX. The method further includes isomerizing at least a portion of the MX, the OX, or both from the xylene-containing composition (xylene-containing effluent 22). Isomerizing MS, OX, or both to PX may include passing at least a portion of the xylene-containing composition to the membrane isomerization unit 120. The membrane isomerization unit 120 may include any of the features previously described in this disclosure for the membrane isomerization unit 120. The method further includes dealkylating at least a portion of the EB from the xylene-containing composition to form one or more $C_{7-}$ compounds. The method further includes subjecting at least a portion of the xylene-containing composition to the membrane separation unit 140 to produce the permeate 142 that is PX-rich and the retentate 144 that is PX-lean. The membrane separation unit 140 may include any of the features the membrane separation unit 140 previously described in this disclosure. The method further includes recovering PX from the xylene-containing composition, the permeate composition, or both in the PX-recovery unit 110 to produce a PX product (PX product 112). The PX-recovery unit 110 may include any of the features of the PX-recovery unit 110 previously described in this disclosure.

The method may further include subjecting at least a second portion of the xylene-containing composition to a separation process operable to separate at least a portion of the $C_{7-}$ compounds from the at least a second portion of the xylene-containing composition. In some embodiments, the $C_{7-}$ compounds are separated from the at least a second portion of the xylene-containing composition using the stripper 150. The stripper 150 may include any of the features of the stripper 150 previously described in this disclosure. In some embodiments, dealkylating the at least a portion of the EB may include contacting the at least a portion of the EB with a dealkylation catalyst in the EB dealkylation unit 130. The EB dealkylation unit 130 may include any of the features of the EB dealkylation unit 130 previously described in this disclosure. In some embodiments, recovering PX includes subjecting at least a third portion of the xylene-containing composition to crystallization, selective adsorption, or combinations of these to recover the p-xylene product. In some embodiments, the PX product may include at least 99.0 wt. % PX.

In some embodiments, another method for producing PX from a $C_8$ aromatics-containing stream may include separating the $C_8$ aromatic-containing composition to produce a xylene-containing composition (xylene-containing effluent 22) and a heavy composition (heavy stream 24), and passing the xylene-containing composition (xylene-containing effluent 22) to the xylene-processing loop 102. The xylene-processing loop 102 includes the PX-recovery unit 110, the membrane isomerization unit 120, the EB dealkylation unit 130, the membrane separation unit 140, and the stripper 150. As previously discussed in this disclosure, the PX-recovery unit 110 may be operable to produce the PX product 112, which is passed out of the xylene processing loop 102, the membrane isomerization unit 120 may be operable to isomerize a portion of the MX, OX, and optionally EB from the xylene-containing effluent 22 to PX, the EB dealkylation unit 130 may be operable to dealkylate at least a portion of EB from the xylene-containing effluent 22 to $C_{7-}$ compounds, and the membrane separation unit 140 may be operable to separate a portion of the xylene-containing effluent 22 into the permeate 142 that is PX-rich and the retentate 144 that is PX-lean. A plurality of configurations of the xylene processing loop 102 will now be described in further detail in reference to FIGS. 2-6.

Figure 4:
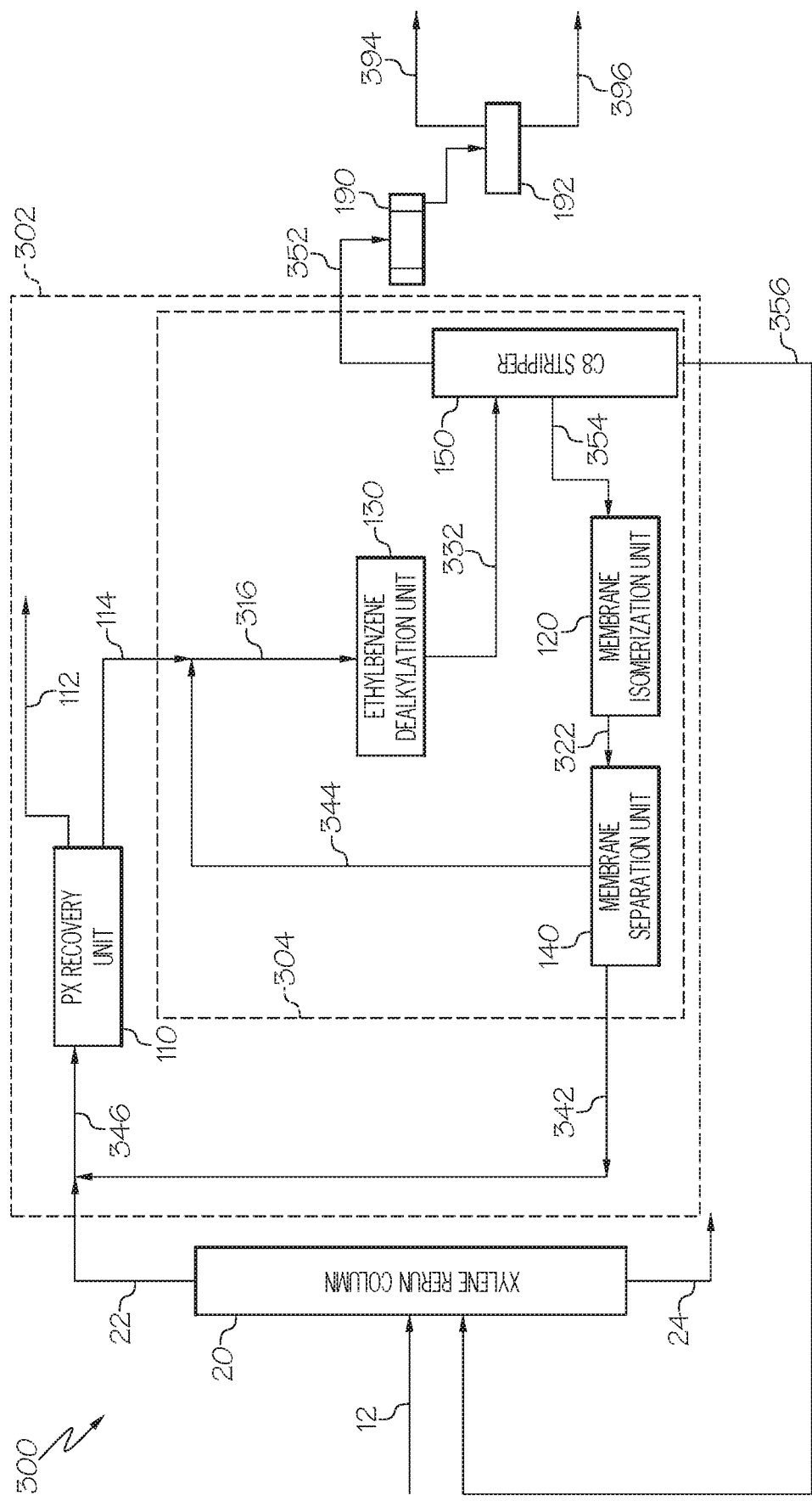
FIG. 4 schematically depicts a process flow diagram for yet another embodiment of a system for producing p-xylene from a $C_8$-containing stream, according to one or more embodiments described in this disclosure.
Figure 5:
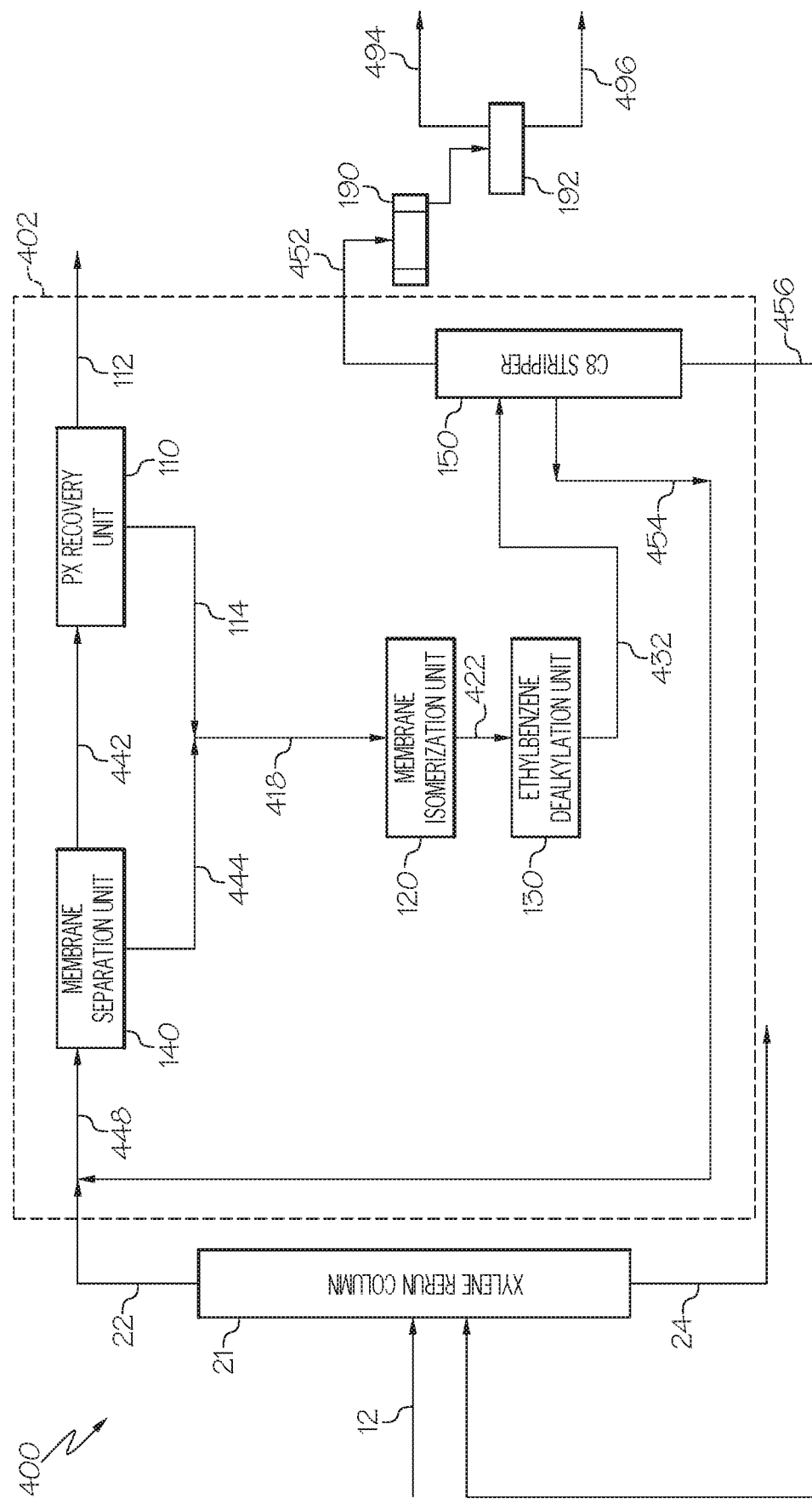
FIG. 5 schematically depicts a process flow diagram for another embodiment of a system for producing p-xylene from a $C_8$-containing stream, according to one or more embodiments described in this disclosure.

Referring now to FIGS. 2-4, the xylene processing loop 102 of system 100 may include the PX-recovery unit 110 positioned directly downstream of the xylene rerun column 20 so that the xylene-containing effluent 22 may be passed directly from the xylene rerun column 20 to the PX-recovery unit 110. For FIGS. 2-4, the PX-recovery unit 110 is the first unit in the xylene processing loop 102, and the membrane isomerization unit 120, EB dealkylation unit 130, membrane separation unit 140, and stripper 150 are all considered to be downstream of the PX-recovery unit 110. The PX-recovery unit 110, membrane isomerization unit 120, EB dealkylation unit 130, membrane separation unit 140, and stripper 150 may include any of the features and operating conditions previously described in this disclosure for each of these units. In some embodiments, the xylene-containing effluent 22 may be combined with the permeate 142 to form a combined PX recovery feed 146, which may be passed to the PX-recovery unit 110. In other embodiments, the xylene-containing effluent 22 and the permeate 142 may be passed individually to the PX-recovery unit 110 and mixed within the PX-recovery unit 110. The PX-recovery unit 110 separates the xylene-containing effluent 22, permeate 142, or both into the PX product 112 and the PX-depleted effluent 114. The PX product 112 may be passed out of the xylene processing loop 102. The PX product 112 may be recovered as a product or further processed, such as by further purifying the PX or by passing the PX product 112 to a downstream process as an intermediate to make one or more other products.

Referring to FIG. 2, the PX-depleted effluent 114 may be passed directly from the PX-recovery unit 110 to the membrane isomerization unit 120. The PX-depleted effluent 114 may have a concentration of PX less than the concentration of PX in the xylene-containing effluent 22, the permeate 142, or the combined PX recovery feed 146. The PX-depleted effluent 114 may also include the MX, OX, and EB from the xylene-containing effluent 22, the permeate 142, or both. In some embodiments, the PX-depleted effluent 114 may be combined with the retentate 144 from the membrane separation unit 140 to form combined isomerization feed 116, which may then be passed to the membrane isomerization unit 120. In other embodiments, the PX-depleted effluent 114 and the retentate 144 may be independently passed to the membrane isomerization unit 120. The membrane isomerization unit 120 may be operable to isomerize at least a portion of the MX, OX, EB, or combinations of these in the PX-depleted effluent 114, the retentate 144, or both to PX to produce the isomerate 122. The isomerate 122 may have a concentration of PX greater than the concentration of PX in the PX-depleted effluent 114. Additionally, the isomerate 122 may have concentrations of MX, OX, and EB less than the concentrations of MX, OX, and EB, respectively, in the PX-depleted effluent 114.

The isomerate 122 may be passed from the membrane isomerization unit 120 to the EB dealkylation unit 130. In some embodiments, the isomerate 122 may be passed directly from the membrane isomerization unit 120 to the EB dealkylation unit 130 without any intervening operations or processes. The EB dealkylation unit 130 may be operable to contact the isomerate 122 with the dealkylation catalyst under conditions sufficient to convert at least a portion of the EB in the isomerate 122 to one or more $C_{7-}$ compounds. The dealkylation effluent 132 may be passed out of the EB dealkylation unit 130. The dealkylation effluent 132 may have a concentration of EB less than a concentration of EB in the isomerate 122.

Referring still to FIG. 2, the dealkylation effluent 132 may be passed to the stripper 150, which may be operable to remove the $C_{7-}$ compounds from the dealkylation effluent 132. For example, the stripper 150 may be operable to separate the dealkylation effluent 132 into the $C_{7-}$ effluent 152, the EB-depleted effluent 154, and the stripper bottoms 156. The $C_{7-}$ effluent 152 includes compounds having a boiling point temperature greater than the $C_8$ aromatics and includes the $C_{7-}$ compounds from the dealkylation effluent 132. The $C_{7-}$ effluent 152 may be passed out of the stripper 150, thereby passing the $C_{7-}$ effluent 152 out of the xylene processing loop 102. The stripper bottoms 156 may include compounds having boiling point temperatures less than the boiling point temperature of the $C_8$ aromatics. The stripper bottoms 156 may be recycled back to the xylene rerun column 20 and ultimately removed from the system 100 through the heavy stream 24. The EB-depleted effluent 154 may be a side draw from the stripper 150 and may include the $C_8$ aromatics from the dealkylation effluent 132 (PX, MX, OX, EB).

The EB-depleted effluent 154 may be passed from the stripper 150 to the membrane separation unit 140. In some embodiments, the EB-depleted effluent 154 may be passed directly from the stripper 150 to the membrane separation unit 140 without passing through any intervening operations. The membrane separation unit 140 may be operable to contact the EB-depleted effluent 154 with a carbon-based membrane to separate the EB-depleted effluent 154 into the permeate 142, which is PX-rich, and the retentate 144, which is PX-lean. The permeate 142 may be passed to the PX-recovery unit 110 for recovery of the PX from the permeate 142. In some embodiments, the permeate 142 may be combined with the xylene-containing effluent 22 upstream of the PX-recovery unit 110 prior to being passed to the PX-recovery unit 110. In other embodiments the permeate 142 may be passed to the PX-recovery unit 110 independently of the xylene-containing effluent 22.

The retentate 144 may be passed back to the membrane isomerization unit 120 to complete a secondary nested loop, which is referred to in this disclosure as xylene isomerization loop 104. Passing the retentate 144 to the membrane isomerization unit 120 bypasses the PX-recovery unit 110 to recycle the greater concentrations of MX, OX and EB from the EB-depleted effluent 154 back through the xylene isomerization loop 104. This reduces the MX, OX, and EB that is recycled back through PX-recovery unit 110, which may further reduce the size and energy requirements of the PX-recovery unit 110. As previously discussed, the retentate 144 may be combined with the PX-depleted effluent 114 to form the combined isomerization feed 116, or the retentate 144 and the PX-depleted effluent 114 may be passed independently to the membrane isomerization unit 120.

Referring again to FIG. 2, in some embodiments, a method for producing PX from a $C_8$-aromatic-containing composition 12 may include introducing a $C_8$-aromatic-containing composition 12 to the xylene rerun column 20 operable to separate the $C_8$-aromatic-containing composition 12 into the xylene-containing effluent 22 and the heavy effluent 24. The xylene-containing effluent 22 includes at least PX and one or more of OX, MX, EB, or combinations of these. The method further includes passing at least a portion of the xylene-containing effluent 22 to the PX recovery unit 110 to separate at least a portion of the xylene-containing effluent 22 into the PX product 112 and the PX-depleted effluent 114. The method may further include recovering the PX product 112 from the PX recovery unit 110 and passing the PX-depleted effluent 114 through a xylene isomerization loop 104, the xylene isomerization loop 104 including the membrane isomerization unit 120, the EB dealkylation unit 130, the membrane separation unit 140, and the stripper 150. The membrane isomerization unit 120, the EB dealkylation unit 130, the membrane separation unit 140, and the stripper 150 may have any of the features discussed previously in this disclosure for these units. The method may further include passing the permeate 142 from the membrane separation unit 140 back to the PX recovery unit 110 and passing the retentate 144 from the membrane separation unit 140 through the xylene isomerization loop 104. The method may further include passing the dealkylation effluent 132 from the ethylbenzene dealkylation unit 130 to the stripper 150, the dealkylation effluent 132 comprising the one or more $C_{7-}$ compounds, and passing a $C_{7-}$ effluent 152 out of the stripper 150, where passing the $C_{7-}$ effluent 152 out of the stripper 150 removes at least a portion of the $C_{7-}$ compounds from the xylene isomerization loop 104.

The method may further include passing the PX-depleted effluent 114 from the PX recovery unit 110 directly to the membrane isomerization unit 120 and passing the PX-depleted effluent 114 through a catalytic membrane in the membrane isomerization unit 120, which causes isomerization of at least a portion of the MX, OX, EB, or combinations of these in the PX-depleted effluent 114 to PX to produce the isomerate 122 having a concentration of PX greater than the concentration of PX in the PX-depleted effluent 114. The method may further include passing the isomerate 122 from the membrane isomerization unit 120 to the EB dealkylation unit 130, and contacting the isomerate 122 with a dealkylation catalyst, which causes dealkylation of at least a portion of the EB in the isomerate 122 to produce a dealkylation effluent 132 that includes the $C_{7-}$ compounds and has a concentration of EB that is less than a concentration of EB in the isomerate 122. The method may further include passing the dealkylation effluent 132 to the stripper 150 to separate the dealkylation effluent 132 into the $C_{7-}$ effluent 152 and the EB-depleted effluent 154, passing the $C_{7-}$ effluent 152 out of the stripper 150, and passing the EB-depleted effluent 154 out of the stripper. The method may further include passing the EB-depleted effluent 154 to the membrane separation unit 140, passing the EB-depleted effluent 154 into contact with a carbon-based membrane, which causes separation of the EB-depleted effluent 154 into the permeate 142 and the retentate 144, and passing the retentate 144 back to the membrane isomerization unit 120.

Referring now to FIG. 3, a system 200 for producing PX from a $C_8$-aromatic containing stream is depicted. System 200 is similar to system 100 of FIG. 2, except that in the xylene isomerization loop 204, the membrane separation unit 140 is disposed between the membrane isomerization unit 120 and the EB dealkylation unit 130. Referring to FIG. 3, in system 200, the $C_8$-aromatic-containing composition 12 is introduced to the xylene rerun column 20, which is operable to separate the $C_8$-aromatic-containing composition 12 into the xylene-containing effluent 22 and the heavy stream 24. The xylene-containing effluent 22 is passed to a xylene processing loop 202, which includes the PX-recovery unit 110, the membrane isomerization unit 120, the EB dealkylation unit 130, the membrane separation unit 140, and stripper 150. The PX-recovery unit 110, the membrane isomerization unit 120, the EB dealkylation unit 130, the membrane separation unit 140, and the stripper 150 may have any of the features and operating conditions previously described in this disclosure in relation to FIG. 2. Referring again to FIG. 3, the xylene-containing effluent 22 is passed to the PX-recovery unit 110. The xylene-containing effluent 22 may be combined with a permeate 242 from the membrane separation unit 140 to form a combined PX recovery feed 246, which is then passed to the PX-recovery unit 110. Alternatively, the xylene-containing effluent 22 may be passed to the PX-recovery unit 110 independent of the permeate 242. The PX-recovery unit 110 separates the xylene-containing effluent 22, permeate 242, or both into the PX product 112 and the PX-depleted effluent 114. The PX product 112 may be passed out of the xylene processing loop 202.

Referring to FIG. 3, the PX-depleted effluent 114 may be passed directly from the PX-recovery unit 110 to the membrane isomerization unit 120. The PX-depleted effluent 114 may have a concentration of PX less than the concentration of PX in the xylene-containing effluent 22, the permeate 242, or the combined PX recovery feed 246. The PX-depleted effluent 114 may also include the MX, OX, and EB from the xylene-containing effluent 22, the permeate 242, or both. The PX-depleted effluent 114 may be combined with the EB-depleted effluent 254 from the stripper 150 to form a combined isomerization feed 216, which may then be passed to the membrane isomerization unit 120. In some embodiments, the PX-depleted effluent 114 and the EB-depleted effluent 254 may be independently passed to the membrane isomerization unit 120. The membrane isomerization unit 120 may be operable to isomerize at least a portion of the MX, OX, EB, or combinations of these in the PX-depleted effluent 114, the EB-depleted effluent 254, or both to PX to produce an isomerate 222. The isomerate 222 may have a concentration of PX greater than the concentration of PX in the PX-depleted effluent 114. Additionally, the isomerate 222 may have concentrations of MX, OX, and EB less than the concentrations of MX, OX, and EB, respectively, in the PX-depleted effluent 114.

The membrane separation unit 140 may be directly downstream of the membrane isomerization unit 120 so that the isomerate 222 may be passed from the membrane isomerization unit 120 to the membrane separation unit 140. In some embodiments, the isomerate 222 may be passed directly from the membrane isomerization unit 120 to the membrane separation unit 140 without passing through any intervening unit operations or processes. The membrane separation unit 140 may be operable to contact the isomerate 222 with a carbon-based membrane to separate the isomerate 222 into a permeate 242, which is PX-rich, and a retentate 244, which is PX-lean. The permeate 242 may be passed back to the PX-recovery unit 110 for recovery of the PX from the permeate 242. In some embodiments, the permeate 242 may be combined with the xylene-containing effluent 22 upstream of the PX-recovery unit 110 prior to being passed to the PX-recovery unit 110. In other embodiments the permeate 242 may be passed to the PX-recovery unit 110 independently of the xylene-containing effluent 22.

Referring again to FIG. 3, the EB dealkylation unit 130 may be directly downstream of the membrane separation unit 140 so that the retentate 244 may be passed from the membrane separation unit 140 to the EB dealkylation unit 130. In some embodiments, the retentate 244 may be passed directly from the membrane separation unit 140 to the EB dealkylation unit 130 without any intervening operations or processes. The EB dealkylation unit 130 may be operable to contact the retentate 244 with the dealkylation catalyst under conditions sufficient to convert at least a portion of the EB in the retentate 244 to one or more $C_{7-}$ compounds to produce a dealkylation effluent 232, which may have a concentration of EB less than a concentration of EB in the retentate 244. Dealkylation effluent 232 may be passed out of EB dealkylation unit 130.

Referring still to FIG. 3, the dealkylation effluent 232 may be passed to the stripper 150, which may be operable to remove the $C_{7-}$ compounds from the dealkylation effluent 232. The stripper 150 may be operable to separate the dealkylation effluent 232 into the $C_{7-}$ effluent 252, the EB-depleted effluent 254, and the stripper bottoms 256. The $C_{7-}$ effluent 252, which includes the $C_{7-}$ compounds from the dealkylation effluent 232 and other constituents having boiling point temperatures less than the $C_8$ aromatics, may be passed out of the stripper 150, thereby passing the $C_{7-}$ compounds out of the xylene processing loop 102. The $C_{7-}$ effluent 252 may be further processed in the condenser 190 and supplemental separator 192 to produce a light gas stream 294 and a light aromatic stream 296. The stripper bottoms 256, which includes constituents of the dealkylation effluent 232 having boiling temperatures greater than the $C_8$ aromatics, may be recycled back to the xylene rerun column 20. The EB-depleted effluent 254 may be a side draw from the stripper 150 and may include the $C_8$ aromatics from the dealkylation effluent 132 (PX, MX, OX, and EB). The EB-depleted effluent 254 may be passed back to the membrane isomerization unit 120 to complete a secondary nested processing loop, which is referred to in this disclosure as xylene isomerization loop 204. Passing the EB-depleted effluent 254 to the membrane isomerization unit 120 bypasses the PX-recovery unit 110 to recycle the greater concentrations of MX, OX and EB from the EB-depleted effluent 254 back through the xylene isomerization loop 204. This reduces the MX, OX, and EB that is recycled back through PX-recovery unit 110, which may further reduce the size and energy requirements of the PX-recovery unit 110.

Referring again to FIG. 3, another embodiment of a method for producing PX from the $C_8$-aromatic-containing composition 12 may include introducing the $C_8$-aromatic-containing composition 12 to the xylene rerun column 20 operable to separate the $C_8$ aromatic-containing composition 21 into the xylene-containing effluent 22 and the heavy effluent 24. The xylene-containing effluent 22 includes PX and one or more of OX, MX, EB, or combinations of these. The method further includes passing at least a portion of the xylene-containing effluent 22 to the PX recovery unit 110 to separate at least a portion of the xylene-containing effluent 22 into the PX product 112 and the PX-depleted effluent 114. The method may further include recovering the PX product 112 from the PX recovery unit 110 and passing the PX-depleted effluent 114 through a xylene isomerization loop 204, the xylene isomerization loop 204 including the membrane isomerization unit 120, the EB dealkylation unit 130, the membrane separation unit 140, and the stripper 150. The membrane isomerization unit 120, the EB dealkylation unit 130, the membrane separation unit 140, and the stripper 150 may have any of the features discussed previously in this disclosure for these units. The method may further include passing the permeate 242 from the membrane separation unit 140 back to the PX recovery unit 110 and passing the retentate 244 from the membrane separation unit 140 through the xylene isomerization loop 204. The method may further include passing the dealkylation effluent 232 from the ethylbenzene dealkylation unit 130 to the stripper 150, the dealkylation effluent 232 comprising the one or more $C_{7-}$ compounds, and passing a $C_{7-}$ effluent 252 out of the stripper 150, where passing the $C_{7-}$ effluent 252 out of the stripper 150 removes at least a portion of the $C_{7-}$ compounds from the xylene isomerization loop 204.

In some embodiments, the method may include passing the PX-depleted effluent 114 from the PX recovery unit 110 directly to the membrane isomerization unit 120, and passing the PX-depleted effluent 114 through a catalytic membrane in the membrane isomerization unit 120, which causes isomerization of at least a portion of the MX, OX, EB, or combinations of these in the PX-depleted effluent 114 to PX to produce the isomerate 222 having a concentration of PX greater than the concentration of PX in the PX-depleted effluent 114. In some embodiments, the method may further include passing the isomerate 222 from the membrane isomerization unit 120 to the membrane separation unit 140, and passing the isomerate 222 through a membrane, which causes separation of the isomerate 222 into the permeate 242 and the retentate 244, the permeate 242 having a concentration of PX greater than the concentration of PX in the retentate 244. In some embodiments, the method may further include passing the retentate 244 to the EB dealkylation unit 130, and contacting the retentate 244 with a dealkylation catalyst, which causes dealkylation of at least a portion of the EB in the retentate 244 to produce a dealkylation effluent 232 that includes one or more $C_{7-}$ compounds and a concentration of EB less than a concentration of EB in the retentate 244. In some embodiments, the method may further include passing the dealkylation effluent 232 to the stripper 150 which may be operable to separate the dealkylation effluent 232 into at least a $C_{7-}$ effluent and an EB-depleted effluent 254. The method may further include passing the $C_{7-}$ effluent 252 out of the stripper 150, the $C_{7-}$ effluent 252 comprising at least a portion of the $C_{7-}$ compounds from the dealkylation effluent 232. The method may further include passing the EB-depleted effluent 254 from the stripper 150 back to the membrane isomerization unit 120, the EB-depleted effluent 254 having a concentration of EB less than the concentration of EB in the retentate 244.

Referring now to FIG. 4, another system 300 for producing PX from a $C_8$-aromatic containing stream is depicted. System 300 is similar to system 100 of FIG. 2 and system 200 of FIG. 3, except that the EB dealkylation unit 130 is directly downstream of the PX-recovery unit 110 so that the PX product 112 is passed from the PX-recovery unit 110 to the EB dealkylation unit 130, and the membrane isomerization unit 120 and membrane separation unit 140 are both downstream of the EB dealkylation unit 130 in the xylene isomerization loop 304. Referring to FIG. 4, in system 300, the $C_8$-aromatic-containing composition 12 is introduced to the xylene rerun column 20, which is operable to separate the $C_8$-aromatic-containing composition 12 into the xylene-containing effluent 22 and the heavy stream 24. The xylene-containing effluent 22 is passed to an xylene processing loop 302, which includes the PX-recovery unit 110, the membrane isomerization unit 120, the EB dealkylation unit 130, the membrane separation unit 140, and stripper 150. The PX-recovery unit 110, the membrane isomerization unit 120, the EB dealkylation unit 130, the membrane separation unit 140, and the stripper 150 may have any of the features and operating conditions previously described in this disclosure in relation to FIG. 2. As shown in FIG. 4, the xylene-containing effluent 22 is passed to the PX-recovery unit 110. The xylene-containing effluent 22 may be combined with a permeate 342 from the membrane separation unit 140 prior to passing a combined PX recovery feed 346 to the PX-recovery unit 110 or may be passed to the PX-recovery unit 110 independent of the permeate 342. The PX-recovery unit 110 separates the xylene-containing effluent 22, permeate 342, or both into the PX product 112 and the PX-depleted effluent 114. The PX product 112 may be passed out of the xylene processing loop 302.

Referring to FIG. 4, the PX-depleted effluent 114 may be passed directly from the PX-recovery unit 110 to the EB dealkylation unit 130. The PX-depleted effluent 114 may have a concentration of PX less than the concentration of PX in the xylene-containing effluent 22, the permeate 342, or the combined PX recovery feed 346. The PX-depleted effluent 114 may also include the MX, OX, and EB from the xylene-containing effluent 22, the permeate 342, or both. The PX-depleted effluent 114 may be combined with the retentate 344 from the membrane separation unit 140 to form a combined isomerization feed 316, which may then be passed to the EB dealkylation unit 130. In some embodiments, the PX-depleted effluent 114 and the retentate 344 may be independently passed to the EB dealkylation unit 130. The EB dealkylation unit 130 may be operable to contact the PX-depleted effluent 114, the retentate 344, or both with the dealkylation catalyst under conditions sufficient to convert at least a portion of the EB in the PX-depleted effluent 114, retentate 344, or both to one or more $C_{7-}$ compounds to produce a dealkylation effluent 332, which may have a concentration of EB less than a concentration of EB in the PX-depleted effluent 114, the retentate 344, or the combined PX recovery feed 346. The dealkylation effluent 332 may be passed out of the EB dealkylation unit 130.

Referring still to FIG. 4, the dealkylation effluent 332 may be passed to the stripper 150, which may be operable to remove the $C_{7-}$ compounds from the dealkylation effluent 332. The stripper 150 may be operable to separate the dealkylation effluent 332 into the $C_{7-}$ effluent 352, the EB-depleted effluent 354, and the stripper bottoms 356. The $C_{7-}$ effluent 352, which includes the $C_{7-}$ compounds from the dealkylation effluent 332 and other constituents having boiling point temperatures less than the $C_8$ aromatics, may be passed out of the stripper 150, by which the $C_{7-}$ compounds are passed out of the xylene processing loop 302. The $C_{7-}$ effluent 352 may be further processed in the condenser 190 and supplemental separator 192 to produce a light gas stream 394 and a light aromatic stream 396, which may include the benzene and toluene from EB dealkylation. The stripper bottoms 356, which includes constituents of the dealkylation effluent 332 having boiling temperatures greater than the $C_8$ aromatics, may be recycled back to the xylene rerun column 20. The EB-depleted effluent 354 may be a side draw from the stripper 150 and may include the $C_8$ aromatics from the dealkylation effluent 332 (PX, MX, OX, EB).

The membrane isomerization unit 120 may be disposed downstream of the stripper 150 so that the EB-depleted effluent 354 may be passed from the stripper 150 to the membrane isomerization unit 120. In some embodiments, the EB-depleted effluent 354 may be passed directly from the stripper 150 to the membrane isomerization unit 120 without passing through any intervening unit operations or processes. The membrane isomerization unit 120 may be operable to isomerize at least a portion of the MX, OX, EB, or combinations of these in the EB-depleted effluent 354 to PX to produce an isomerate 322. The isomerate 322 may have a concentration of PX greater than the concentration of PX in the EB-depleted effluent 354. Additionally, the isomerate 322 may have concentrations of MX, OX, and EB less than the concentrations of MX, OX, and EB, respectively, in the EB-depleted effluent 354.

The membrane separation unit 140 may be directly downstream of the membrane isomerization unit 120 so that the isomerate 322 may be passed from the membrane isomerization unit 120 to the membrane separation unit 140. In some embodiments, the isomerate 322 may be passed directly from the membrane isomerization unit 120 to the membrane separation unit 140 without passing through any intervening unit operations or processes. The membrane separation unit 140 may be operable to contact the isomerate 322 with a carbon-based membrane to separate the isomerate 322 into a permeate 342, which is PX-rich, and a retentate 344, which is PX-lean. The permeate 342 may be passed back to the PX-recovery unit 110 for recovery of the PX from the permeate 342. In some embodiments, the permeate 342 may be combined with the xylene-containing effluent 22 upstream of the PX-recovery unit 110 prior to being passed to the PX-recovery unit 110. In other embodiments the permeate 342 may be passed to the PX-recovery unit 110 independently of the xylene-containing effluent 22. The retentate 344 may be passed back to the EB dealkylation unit 130 to complete xylene isomerization loop 304. Passing the retentate 344 to the EB dealkylation unit 130 bypasses the PX-recovery unit 110 to recycle the greater concentrations of MX, OX, and EB from the retentate 344 back through the xylene isomerization loop 304. This reduces the MX, OX, and EB that is recycled back through PX-recovery unit 110, which may further reduce the size and energy requirements of the PX-recovery unit 110.

Referring still to FIG. 4, another embodiment of a method for producing PX from the $C_8$-aromatic-containing composition 12 may include introducing the $C_8$-aromatic-containing composition 12 to the xylene rerun column 20 operable to separate the $C_8$ aromatic-containing composition 21 into the xylene-containing effluent 22 and the heavy effluent 24. The xylene-containing effluent 22 includes PX and one or more of OX, MX, EB, or combinations of these. The method further includes passing at least a portion of the xylene-containing effluent 22 to the PX recovery unit 110 to separate at least a portion of the xylene-containing effluent 22 into the PX product 112 and the PX-depleted effluent 114. The method may further include recovering the PX product 112 from the PX recovery unit 110 and passing the PX-depleted effluent 114 through the xylene isomerization loop 304, which includes the membrane isomerization unit 120, the EB dealkylation unit 130, the membrane separation unit 140, and the stripper 150. The membrane isomerization unit 120, the EB dealkylation unit 130, the membrane separation unit 140, and the stripper 150 may have any of the features and operating conditions previously discussed in this disclosure in relation to FIG. 2. The method may further include passing the permeate 342 from the membrane separation unit 140 back to the PX recovery unit 110 and passing the retentate 344 from the membrane separation unit 140 back through the xylene isomerization loop 304. The method may further include passing the dealkylation effluent 332 from the ethylbenzene dealkylation unit 130 to the stripper 150, the dealkylation effluent 332 comprising the one or more $C_{7-}$ compounds, and passing a $C_{7-}$ effluent 352 out of the stripper 150, where passing the $C_{7-}$ effluent 352 out of the stripper 150 removes at least a portion of the $C_{7-}$ compounds from the xylene isomerization loop 304.

In some embodiments, the method may further include passing the PX-depleted effluent 114 from the PX recovery unit 110 directly to the EB dealkylation unit 130, and contacting the PX-depleted effluent 114 with a dealkylation catalyst, which may cause dealkylation of at least a portion of the EB in the PX-depleted effluent 114 to produce a dealkylation effluent 332. The dealkylation effluent 332 may include the one or more $C_{7-}$ compounds and a concentration of EB less than a concentration of EB in the PX-depleted effluent 114. In some embodiments, the method may further include passing the dealkylation effluent 332 to the stripper 150, which is operable to separate the dealkylation effluent 332 into at least a $C_{7-}$ effluent 352 and an EB-depleted effluent 354. The method may include passing the $C_{7-}$ effluent 352 out of the stripper 150, the $C_{7-}$ effluent 352 comprising at least a portion of the $C_{7-}$ compounds from the dealkylation effluent 332. The method may include passing the EB-depleted effluent 354 from the stripper 150 to the membrane isomerization unit 120, the EB-depleted effluent 354 having a concentration of EB less than the concentration of EB in the PX-depleted effluent 114. In some embodiments, the method may include passing the EB-depleted effluent 354 from the stripper 150 to the membrane isomerization unit 120, and passing the EB-depleted effluent 354 through a catalytic membrane in the membrane isomerization unit 120, which may cause isomerization of at least a portion of the MX, OX, EB, or combinations of these in the EB-depleted effluent 354 to PX to produce an isomerate 322 having a concentration of PX greater than a concentration of PX in the EB-depleted effluent 354. In some embodiments, the method may further include passing the isomerate 322 to the membrane separation unit 140 and passing the isomerate 322 through a membrane of the membrane separation unit 140, which may cause separation of the isomerate 322 into the permeate 342 and the retentate 344, the permeate 342 having a concentration of PX greater than the concentration of PX in the retentate 344. The method may further include passing the permeate 342 to the PX recovery unit 110.

Referring now to FIG. 5, still another system 400 for producing PX from the $C_8$-aromatic-containing composition 12 is depicted in which the xylene-containing effluent 22 from the xylene rerun column 20 is first passed to the membrane separation unit 140 before being passed to the PX-recovery unit 110. In system 400, the membrane separation unit 140 may be the first unit of the xylene processing loop 402, and the PX-recovery unit 110 may be immediately downstream of the membrane separation unit 140. The membrane separation unit 140 separates the xylene-containing effluent 22 into a permeate 442 that is PX-rich and a retentate 444 that is PX-lean. The permeate 442 may be passed to the PX-recovery unit 110 while the retentate 444 is passed to the next unit operation in the xylene processing loop 402. One or more streams from the xylene processing loop 402 may be recycled back to the membrane separation unit 140 for separation into the permeate 442 and retentate 444 so that only the permeate 442, which is PX-rich, is passed to the PX-recovery unit 110.

Referring to FIG. 5, in system 400, the $C_8$-aromatic-containing composition 12 is introduced to the xylene rerun column 20, which is operable to separate the $C_8$-aromatic-containing composition 12 into at least the xylene-containing effluent 22 and the heavy stream 24. The xylene-containing effluent 22 is then passed to the xylene processing loop 402, which includes the membrane separation unit 140, the PX-recovery unit 110, the membrane isomerization unit 120, the EB dealkylation unit 130, and the stripper 150. The PX-recovery unit 110, the membrane isomerization unit 120, the EB dealkylation unit 130, the membrane separation unit 140, and the stripper 150 may have any of the features and operating conditions previously described in this disclosure in relation to FIG. 2. The membrane separation unit 140 may be directly downstream of the xylene rerun column 20 so that the xylene-containing effluent 22 may be passed from the xylene rerun column 20 to the membrane separation unit 140. In some embodiments, the xylene-containing effluent 22 may be passed directly from the xylene rerun column 20 to the membrane separation unit 140 without passing through any intervening unit operations or processes. In some embodiments, the xylene-containing effluent 22 may be combined with an EB-depleted effluent 454 from the stripper 150 to produce a combined stream 448 upstream of the membrane separation unit 140 and the combined stream 448 may be passed to the membrane separation unit 140. In other embodiments, the xylene-containing effluent 22 and the EB-depleted effluent 454 may be passed to the membrane separation unit 140 independent of one another.

Figure 6:
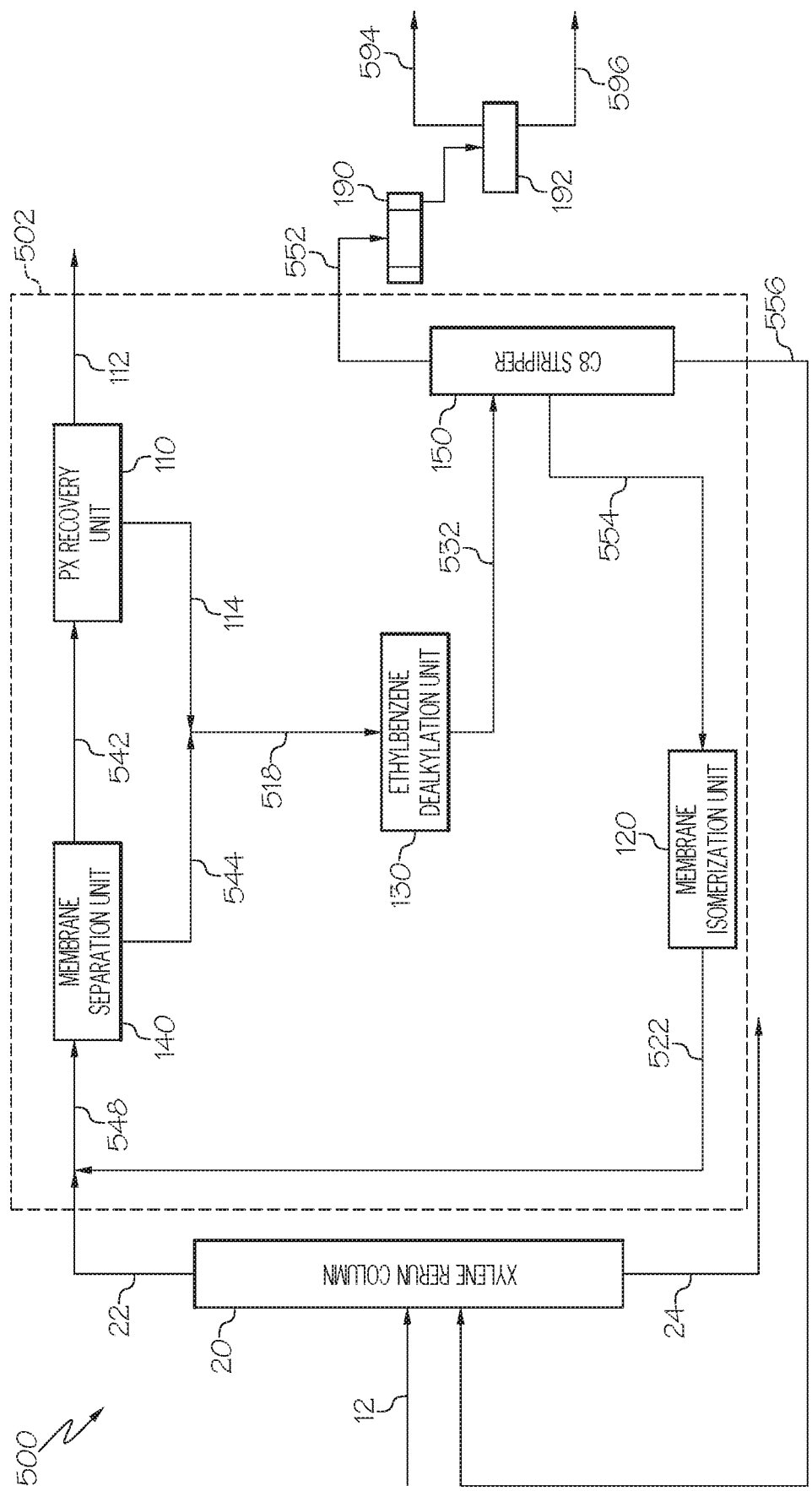
FIG. 6 schematically depicts a process flow diagram for another embodiment of a system for producing p-xylene from a $C_8$-containing stream, according to one or more embodiments described in this disclosure.

The membrane separation unit 140 may be operable to contact the xylene-containing effluent 22, the EB-depleted effluent 454, or both with a carbon-based membrane to separate the xylene-containing effluent 22, the EB-depleted effluent 454, or both into the permeate 442, which has a greater concentration of PX, and the retentate 444, which has a lesser concentration of PX. The permeate 442 may be passed to the PX-recovery unit 110 for recovery of the PX from the permeate 442. In some embodiments, the permeate 442 may be passed directly from the membrane separation unit 140 to the PX-recovery unit 110 without passing to any intervening unit operation or process. The retentate 444 may be passed on to the next unit operation in the xylene processing loop 402, such as the membrane isomerization unit 120 (FIG. 5) or the EB dealkylation unit 130 (FIG. 6). Referring to FIG. 5, in some embodiments, the retentate 444 may be passed from the membrane separation unit 140 to the membrane isomerization unit 120. Passing the permeate 442 having the greater concentration of PX to the PX-recovery unit 110 and bypassing the retentate 444 around the PX-recovery unit 110 may reduce the volume of materials passed to the PX-recovery unit 110, which may reduce the size and energy consumption of the PX-recovery unit 110.

The PX-recovery unit 110 separates the permeate 442 into the PX product 112 and the PX-depleted effluent 114. The PX product 112 may be passed out of the xylene processing loop 402 as a product or intermediate for further processing. Referring again to FIG. 5, in some embodiments, the PX-depleted effluent 114 may be passed from the PX-recovery unit 110 to the membrane isomerization unit 120. The PX-depleted effluent 114 may have a concentration of PX less than the concentration of PX in the permeate 442. The PX-depleted effluent 114 may also include the MX, OX, and EB from the permeate 442. In some embodiments, the PX-depleted effluent 114 and the retentate 444 may be combined to form a combined isomerization feed 418, which may then be passed to the membrane isomerization unit 120. In other embodiments, the PX-depleted effluent 114 and the retentate 444 may be individually passed to the membrane isomerization unit 120 independent of one another. The PX-depleted effluent 114 may be passed directly to the membrane isomerization unit 120 without passing through any intervening unit operations or processes. The retentate 444 may also be passed directly to the membrane isomerization unit 120 without passing through any intervening unit operations or processes.

The membrane isomerization unit 120 may be operable to isomerize at least a portion of the MX, OX, EB, or combinations of these in the PX-depleted effluent 114, retentate 444, or both to PX to produce an isomerate 422. The isomerate 422 may have a concentration of PX greater than the concentration of PX in the PX-depleted effluent 114, retentate 444, or both. Additionally, the isomerate 422 may have concentrations of MX, OX, or EB less than the concentrations of MX, OX, or EB, respectively, in the PX-depleted effluent 114, retentate 444, or both. The isomerate 422 may be passed from the membrane isomerization unit 120 to the EB dealkylation unit 130. In some embodiments, the isomerate 422 may be passed directly from the membrane isomerization unit 120 to the EB dealkylation unit 130 without passing through any intervening unit operations or processes. The EB dealkylation unit 130 may be operable to contact the isomerate 422 with the dealkylation catalyst under conditions sufficient to convert at least a portion of the EB in the isomerate 422 to one or more $C_{7-}$ compounds to produce a dealkylation effluent 432, which may have a concentration of EB less than a concentration of EB in the isomerate 422. Dealkylation effluent 432 may be passed out of EB dealkylation unit 130.

Referring to FIG. 5, the dealkylation effluent 432 may be passed to the stripper 150, which may be operable to remove the $C_{7-}$ compounds from the dealkylation effluent 432. The stripper 150 may be operable to separate the dealkylation effluent 432 into the $C_{7-}$ effluent 452, the EB-depleted effluent 454, and the stripper bottoms 456. The $C_{7-}$ effluent 452, which includes the $C_{7-}$ compounds from the dealkylation effluent 432 and other constituents having boiling point temperatures less than the $C_8$ aromatics, may be passed out of the stripper 150, by which the $C_{7-}$ compounds are passed out of the xylene processing loop 402. The $C_{7-}$ effluent 452 may be further processed in the condenser 190 and supplemental separator 192 to produce a light gas stream 494 and a light aromatic stream 496, which may include the benzene and toluene from EB dealkylation. The stripper bottoms 456, which includes constituents of the dealkylation effluent 432 having boiling temperatures greater than the $C_8$ aromatics, may be recycled back to the xylene rerun column 20. The EB-depleted effluent 454 may be a side draw from the stripper 150 and may include the $C_8$ aromatics from the dealkylation effluent 432 (PX, MX, OX, and EB). The EB-depleted effluent 454 may be passed back to the membrane separation unit 140 to recover the PX converted in the membrane isomerization unit 120 and to further convert MX, OX, and EB in the EB-depleted effluent 454 by passing these constituents back through the xylene processing loop 402.

Referring again to FIG. 5, another embodiment of a method for producing PX from the $C_8$-aromatic-containing composition 12 may include introducing the $C_8$-aromatic-containing composition 12 to the xylene rerun column 20, which is operable to separate the $C_8$-aromatic-containing composition 12 into a xylene-containing effluent 22 and a heavy effluent 24. The xylene-containing effluent 22 may include at least PX and one or more of MX, OX, EB, or combinations of these. The method may further include passing the xylene-containing effluent 22 to the membrane separation unit 140, which may be operable to separate at least a portion of the xylene-containing effluent 22 into the permeate 442 and the retentate 444. The permeate 442 may be PX-rich, and the retentate 444 may be PX-lean. The membrane separation unit 140 may include a carbon-based membrane. The method may include passing the permeate 442 to a PX recovery unit 110 to separate the permeate 442 into a PX product 112 and a PX-depleted effluent 114, recovering the PX product 112 from the PX-recovery unit 110, and passing the PX-depleted effluent 114 and the retentate 444 through a xylene processing loop 402. In addition to the membrane separation unit 140 and the PX-recovery unit 110, the xylene processing loop 402 includes a membrane isomerization unit 120 operable to convert at least a portion of MX, OX, EB, or combinations of these in the PX-depleted effluent 114, retentate 444, or both to PX, an EB dealkylation unit 130 operable to convert EB from the PX-depleted effluent 114, the retentate 444, or both to one or more $C_{7-}$ hydrocarbon compounds, and a stripper 150 operable to remove at least a portion of the one or more $C_{7-}$ compounds from the xylene processing loop 402. The method may further include passing an isomerate 422 from the membrane isomerization unit 120 or an EB-depleted effluent 454 from the stripper 150 back to the membrane separation unit 140. The PX-recovery unit 110, membrane isomerization unit 120, EB dealkylation unit 130, membrane separation unit 140, and stripper 150 may have any of the characteristics or operating conditions previously described in this disclosure in relation to FIG. 2.

Referring again to FIG. 5, in some embodiments, the method may further include passing the PX-depleted effluent 114 and the retentate 444 directly to the membrane isomerization unit 120 and passing the PX-depleted effluent 114 and the retentate 444 through a catalytic membrane in the membrane isomerization unit 120, which causes isomerization of at least a portion of the MX, OX, EB, or combinations of these in the PX-depleted effluent 114, the retentate 444, or both to PX to produce the isomerate 422 having a concentration of PX greater than a concentration of PX in the PX-depleted effluent 114, retentate 444, or both. In some embodiments, the method may further include passing the isomerate 422 from the membrane isomerization unit 120 to the EB dealkylation unit 130, and contacting the isomerate 422 with a dealkylation catalyst, which causes dealkylation of at least a portion of the EB in the isomerate 422 to produce a dealkylation effluent 432 that includes the one or more $C_{7-}$ compounds and a concentration of EB less than a concentration of EB in the isomerate 422. In some embodiments, the method may further include passing the dealkylation effluent 432 to the stripper 150, which may be operable to separate the dealkylation effluent 432 into at least a $C_{7-}$ effluent and an EB-depleted effluent 454, passing the $C_{7-}$ effluent 452 out of the stripper 150, and passing the EB-depleted effluent 454 from the stripper 150 to the membrane isomerization unit 120. The EB-depleted effluent 454 may have a concentration of EB less than the concentration of EB in the isomerate 422. The $C_{7-}$ effluent 452 may include at least a portion of the $C_{7-}$ compounds from the dealkylation effluent 432.

Referring now to FIG. 6, another system 500 for producing PX from the $C_8$-aromatic-containing composition 12 is depicted in which the xylene-containing effluent 22 from the xylene rerun column 20 is first passed to the membrane separation unit 140 before being passed to the PX-recovery unit 110. In system 500, the membrane separation unit 140 is the first unit of the xylene processing loop 502, and the PX-recovery unit 110 may be immediately downstream of the membrane separation unit 140. The membrane separation unit 140 separates the xylene-containing effluent 22 into a permeate 542 that is PX-rich and a retentate 544 that is PX-lean. The permeate 542 may be passed to the PX-recovery unit 110 while the retentate 544 is passed to the next unit operation in the xylene processing loop 402. In system 500 of FIG. 6, the EB dealkylation unit 130 is positioned in the xylene processing loop 502 upstream relative to the membrane isomerization unit 120 so that the retentate 544 is passed directly from the membrane separation unit 140 to the EB dealkylation unit 130. One or more streams from the xylene processing loop 502 may be recycled back to the membrane separation unit 140 for separation into the permeate 542 and retentate 544 so that only the permeate 542 is passed to the PX-recovery unit 110.

Referring to FIG. 6, in system 500, the $C_8$-aromatic-containing composition 12 is introduced to the xylene rerun column 20, which is operable to separate the $C_8$-aromatic-containing composition 12 into at least the xylene-containing effluent 22 and the heavy stream 24. The xylene-containing effluent 22 is then passed to the xylene processing loop 502, which includes the membrane separation unit 140, the PX-recovery unit 110, the EB dealkylation unit 130, the stripper 150, and the membrane isomerization unit 120. The PX-recovery unit 110, the membrane isomerization unit 120, the EB dealkylation unit 130, the membrane separation unit 140, and the stripper 150 may have any of the features and operating conditions previously described in this disclosure in relation to FIG. 2. Referring to FIG. 6, the membrane separation unit 140 may be directly downstream of the xylene rerun column 20 so that the xylene-containing effluent 22 may be passed from the xylene rerun column 20 to the membrane separation unit 140. In some embodiments, the xylene-containing effluent 22 may be passed directly from the xylene rerun column 20 to the membrane separation unit 140 without passing through any intervening unit operations or processes. In some embodiments, the xylene-containing effluent 22 may be combined with an isomerate 522 from the membrane isomerization unit 120 to produce a combined stream 548 upstream of the membrane separation unit 140, and the combined stream 548 may be passed to the membrane separation unit 140. In other embodiments, the xylene-containing effluent 22 and the isomerate 522 may be passed to the membrane separation unit 140 independent of one another.

The membrane separation unit 140 may be operable to contact the xylene-containing effluent 22, the isomerate 522, or both with a carbon-based membrane to separate the xylene-containing effluent 22, the isomerate 522, or both into the permeate 542, which has a greater concentration of PX, and the retentate 544, which has a lesser concentration of PX. The permeate 542 may be passed to the PX-recovery unit 110 for recovery of the PX from the permeate 542. In some embodiments, the permeate 542 may be passed directly from the membrane separation unit 140 to the PX-recovery unit 110 without passing it to any intervening unit operation or process. The retentate 544 may be passed on to the next unit operation in the xylene processing loop 502, such as the EB dealkylation unit 130. In some embodiments, the retentate 544 may be passed from the membrane separation unit 140 to the membrane isomerization unit 120. Passing the permeate 542 having the greater concentration of PX to the PX-recovery unit 110 and bypassing the retentate 544 around the PX-recovery unit 110 may reduce the volume of materials passed to the PX-recovery unit 110, which may reduce the size and energy consumption of the PX-recovery unit 110.

The PX-recovery unit 110 separates the permeate 542 into the PX product 112 and the PX-depleted effluent 114. The PX product 112 may be passed out of the xylene processing loop 502 as a product or intermediate for further processing. Referring again to FIG. 5, in some embodiments, the PX-depleted effluent 114 may be passed from the PX-recovery unit 110 to the EB dealkylation unit 130. The PX-depleted effluent 114 may have a concentration of PX less than the concentration of PX in the permeate 542. The PX-depleted effluent 114 may also include the MX, OX, and EB from the permeate 542. In some embodiments, the PX-depleted effluent 114 and the retentate 544 may be combined to form a combined isomerization feed 518, which may then be passed to the EB dealkylation unit 130. In other embodiments, the PX-depleted effluent 114 and the retentate 544 may be individually passed to the EB dealkylation unit 130 independent of one another. The PX-depleted effluent 114 may be passed directly to the EB dealkylation unit 130 without passing through any intervening unit operations or processes. The retentate 544 may also be passed directly to the EB dealkylation unit 130 without passing through any intervening unit operations or processes.

The EB dealkylation unit 130 may be operable to contact the PX-depleted effluent 114, the retentate 544, or both with the dealkylation catalyst under conditions sufficient to convert at least a portion of the EB in the PX-depleted effluent 114, the retentate 544, or both to one or more $C_{7-}$ compounds to produce a dealkylation effluent 532, which may have a concentration of EB less than a concentration of EB in the PX-depleted effluent 114, the retentate 544, or both. The dealkylation effluent 532 may be passed out of the EB dealkylation unit 130. The dealkylation effluent 532 may be passed to the stripper 150, which may be operable to remove the $C_{7-}$ compounds from the dealkylation effluent 532. The stripper 150 may be operable to separate the dealkylation effluent 532 into the $C_{7-}$ effluent 552, the EB-depleted effluent 554, and the stripper bottoms 556. The $C_{7-}$ effluent 552, which includes the $C_{7-}$ compounds from the dealkylation effluent 532 and other constituents having boiling point temperatures less than the $C_8$ aromatics, may be passed out of the stripper 150, by which the $C_{7-}$ compounds are passed out of the xylene processing loop 502. The $C_{7-}$ effluent 552 may be further processed in the condenser 190 and supplemental separator 192 to produce a light gas stream 594 and a light aromatic stream 596, which may include the benzene and toluene from EB dealkylation. The stripper bottoms 556, which includes constituents of the dealkylation effluent 532 having boiling temperatures greater than the $C_8$ aromatics, may be recycled back to the xylene rerun column 20. The EB-depleted effluent 554 may be a side draw from the stripper 150 and may include the $C_8$ aromatics from the dealkylation effluent 532 (PX, MX, OX, EB).

The EB-depleted effluent 554 may be passed from the stripper 150 to the membrane isomerization unit 120. In some embodiments, the EB-depleted effluent 554 may be passed directly from the stripper 150 to the membrane isomerization unit 120 without passing through any intervening unit operation or process. The membrane isomerization unit 120 may be operable to isomerize at least a portion of the MX, OX, EB, or combinations of these in the EB-depleted effluent 554 to PX to produce an isomerate 522. The isomerate 522 may have a concentration of PX greater than the concentration of PX in the EB-depleted effluent 554. Additionally, the isomerate 522 may have concentrations of MX, OX, or EB less than the concentrations of MX, OX, or EB, respectively, in the EB-depleted effluent 554. The isomerate 522 may be passed from the membrane isomerization unit 120 back to the membrane separation unit 140 to recover the PX converted in the membrane isomerization unit 120 and to further convert MX, OX, and EB present in the isomerate 522 by passing these constituents back through the xylene processing loop 502.

Referring again to FIG. 6, another embodiment of a method for producing PX from the $C_8$-aromatic-containing composition 12 may include introducing the $C_8$-aromatic-containing composition 12 to the xylene rerun column 20, which is operable to separate the $C_8$-aromatic-containing composition 12 into a xylene-containing effluent 22 and a heavy effluent 24. The xylene-containing effluent 22 may include at least PX and one or more of MX, OX, EB, or combinations of these. The method may further include passing the xylene-containing effluent 22 to the membrane separation unit 140, which may be operable to separate at least a portion of the xylene-containing effluent 22 into the permeate 542 and the retentate 544. The permeate 542 may be PX-rich, and the retentate 544 may be PX-lean. The membrane separation unit 140 may include a carbon-based membrane. The method may include passing the permeate 542 to a PX recovery unit 110 to separate the permeate 542 into a PX product 112 and a PX-depleted effluent 114, recovering the PX product 112 from the PX-recovery unit 110, and passing the PX-depleted effluent 114 and the retentate 544 through a xylene processing loop 502. In addition to the membrane separation unit 140 and the PX-recovery unit 110, the xylene processing loop 402 includes a membrane isomerization unit 120 operable to convert at least a portion of MX, OX, EB, or combinations of these in the PX-depleted effluent 114, retentate 544, or both to PX, an EB dealkylation unit 130 operable to convert EB from the PX-depleted effluent 114, the retentate 544, or both to one or more $C_{7-}$ hydrocarbon compounds, and a stripper 150 operable to remove at least a portion of the one or more $C_{7-}$ compounds from the xylene processing loop 502. The method may further include passing an isomerate 522 from the membrane isomerization unit 120 or an EB-depleted effluent 554 from the stripper 150 back to the membrane separation unit 140. The PX-recovery unit 110, membrane isomerization unit 120, EB dealkylation unit 130, membrane separation unit 140, and stripper 150 may have any of the characteristics or operating conditions previously described in this disclosure in relation to FIG. 2.

Referring again to FIG. 6, another embodiment of a method for producing PX from the $C_8$-aromatic-containing composition 12 may include passing the PX-depleted effluent 114 and the retentate 544 directly to the EB dealkylation unit 130 and contacting the PX-depleted effluent 114 and the retentate 544 with a dealkylation catalyst, which causes dealkylation of at least a portion of the EB in the PX-depleted effluent 114, the retentate 544, or both to produce a dealkylation effluent 552 comprising the one or more $C_{7-}$ compounds and a concentration of EB less than a total concentration of EB in the PX-depleted effluent 114, the retentate 544, or the combination of both. The method may further include passing the dealkylation effluent 532 to the stripper 150, which is operable to separate the dealkylation effluent 532 into at least a $C_{7-}$ effluent 532 and an EB-depleted effluent 554. The method may further include passing the $C_{7-}$ effluent 552 out of the stripper 150 and passing the EB-depleted effluent 554 out of the stripper 150. The $C_{7-}$ effluent 552 may include at least a portion of the $C_{7-}$ compounds from the dealkylation effluent 532, and the EB-depleted effluent 554 may have a concentration of EB less than the concentration of EB in the PX-depleted effluent 114, the retentate 544, or the combination of both. The method may further include passing the EB-depleted effluent 554 from the stripper 150 to the membrane isomerization unit 120 and passing the EB-depleted effluent 554 through a catalytic membrane in the membrane isomerization unit 120, which causes isomerization of at least a portion of the MX, OX, EB, or combinations of these in the EB-depleted effluent 554 to PX to produce the isomerate 522 having a concentration of PX greater than a concentration of PX in the EB-depleted effluent 554. The method may further include passing the isomerate 522 back to the membrane separation unit 140.

As previously discussed, the systems and methods described in the present disclosure in relation to FIGS. 2-6 may increase the yield of PX from a stream containing $C_8$ aromatics, such as the $C_8$-aromatic-containing composition 12, by increasing the conversions of MX, OX, and optionally EB to PX. The conversion of MX, OX, and optionally EB can be increased by circulating the unreacted MX, OX, and EB through the xylene isomerization loop 104, 204, 304 or the xylene processing loop 402, 502. The systems and methods described in the present disclosure in relation to FIGS. 2-6 may also decrease the equipment size and power consumption of the PX-recovery unit 110 by diverting unreacted MX, OX, and EB around the PX-recovery unit 110 into the xylene isomerization loop 104, 204, 304 or xylene processing loop 402, 502, thus reducing the volume of constituents passed to the PX-recovery unit 110. Reducing the equipment size and power consumption of the PX-recovery unit 110 may reduce the capital cost and improve the efficiency of the systems 100, 200, 300, 400 and 500.

While FIGS. 2-6 illustrate several possible embodiments of the xylene processing loop 102, 202, 302, 402, 502 having different configurations of the PX-recovery unit 110, membrane isomerization unit 120, EB dealkylation unit 130, membrane separation unit 140, and stripper 150, it is understood that other configurations or arrangements of the PX-recovery unit 110, membrane isomerization unit 120, EB dealkylation unit 130, membrane separation unit 140, and stripper 150 in the xylene processing loop 102 may be possible and these alternative configurations are contemplated as being included as part of the present disclosure.

EXAMPLES

The following examples illustrate the operation of the systems and methods of the present disclosure for producing PX from a $C_8$ aromatic containing stream. The following examples are intended to demonstrate operation of the systems described in the present disclosure and their effects on the size of the PX recovery unit. The Examples are not intended to limit the scope of the present disclosure in any way, in particular with respect to specific mass flow rates, stream compositions, conversion rates, recovery rates, or other assumptions made for purposes of modeling the process.

In the following examples, the conventional system of Comparative Example 1 and the systems of the present disclosure in Examples 2-6 are mathematically modeled using Aspen Plus chemical process modeling software. The $C_8$ aromatic containing composition used for the feed stream to each of Comparative Example 1 and Examples 2-6 has the composition shown in Table 1, which is provided subsequently in this disclosure.

TABLE 1

Composition of $C_8$ aromatics containing composition for Comparative Example 1 and Examples 2-6

| Constituent | Weight Percent (wt. %) |
| --- | --- |
| Toluene | 2.0 |
| EB | 12.5 |
| OX | 17.5 |
| MX | 28.5 |
| PX | 13.5 |
| $C_9$ aromatics | 26.0 |

The PX recovery unit (PX-recovery unit 30 in FIG. 1 and PX-recovery unit 110 in FIGS. 2-6) is a PX crystallization unit having a fixed recovery rate of PX of 65%. The composition of the PX product stream (PX stream 32 in FIG. 1 and PX product 112 in FIGS. 2-6) recovered from the PX recovery unit is assumed to be 99.8 wt. % PX. For Comparative Example 1, the conversion rate of EB in the $C_8$ isomerization unit is assumed to be 70%. For Examples 2-6, the conversion rate of EB in the membrane isomerization unit 120 is assumed to be 0% and the conversion rate of EB in the EB dealkylation unit 130 is assumed to be 70%. For the membrane isomerization unit 120 in Examples 2-6, the conversion rates and selectivity for each of MX, OX, and PX used in the modeling are provided subsequently in this disclosure in Table 2. For the membrane separation unit 140 in Examples 2-6, the separation efficiency of the carbon-based membrane for each of PC, MX, OX, EB, benzene, and toluene are provided subsequently in Table 3. The mass flow rate of the PX product stream (PX stream 32 in FIG. 1 and PX product 112 in FIGS. 2-6) is held constant for the processes of Comparative Example 1 and Examples 2-6.

TABLE 2

Conversion Rate and Selectivity for Membrane Isomerization Unit 120 of Examples 2-6

| Constituent | Conversion (mol %) | Selectivity to MX (%) | Selectivity to OX (%) | Selectivity to PX (%) |
| --- | --- | --- | --- | --- |
| MX | 19.2 | — | 68.6 | 31.4 |
| OX | 33.7 | 52.9 | — | 47.1 |
| PX | 26.3 | 75.8 | 24.2 | — |
| EB | 0 | 0 | 0 | 0 |

TABLE 3

Separation Efficiency for Carbon-Based Membrane in Membrane Separation Unit 140 of Example 2-6

| Constituent | Separation Efficiency (%) |
| --- | --- |
| PX | 80 |
| MX | 20 |
| OX | 20 |
| EB | 20 |
| Benzene | 80 |
| Toluene | 80 |

Comparative Example 1: Conventional PX System 10 of FIG. 1 for Producing PX For Comparative Example 1, the conventional PX system 10 for producing PX illustrated in FIG. 1 and described in conjunction with FIG. 1 is modeled based on the assumptions previously described in the Examples section of this disclosure. The conventional PX system 10 for producing PX includes the PX recovery unit 30 downstream of the xylene rerun column 20, the $C_8$ isomerization unit 40 downstream of the PX-recovery unit 30, and a stripper 50 downstream of the $C_8$ isomerization unit 40. The $C_8$ stream 54 from the stripper 50 is recycled back to the PX-recovery unit 30. The modeling results in the form of the mass flow rates of each constituent in each process stream of FIG. 1 are shown in Table 4, which is provided subsequently in this disclosure. The mass flow rates are rounded to the nearest kilogram per hour (Kg/hr).

TABLE 4

Modeling Data for Comparative Example 1 (all mass flows provided in Kg/hr)

| Stream # | 12 | 24 | 22 | 26 | 32 | 34 |
| --- | --- | --- | --- | --- | --- | --- |
| Light Gas | 0 | 0 | 0 | 0 | 0 | 0 |
| Benzene | 1321 | 0 | 1321 | 1395 | 0 | 1395 |
| Toluene | 0 | 0 | 0 | 16 | 0 | 16 |
| EB | 8255 | 0 | 8291 | 11790 | 7 | 11783 |
| OX | 11557 | 0 | 12022 | 58067 | 21 | 58045 |
| MX | 18822 | 0 | 19854 | 122073 | 43 | 122030 |
| PX | 8916 | 0 | 9375 | 54836 | 35644 | 19193 |
| $C_9$ aromatics | 17171 | 0 | 0 | 0 | 0 | 0 |
| Total Mass Flow | 66042 | 19201 | 50863 | 248178 | 35715 | 212463 |

| Stream # | 42 | 94 | 96 | 54 | 56 |
| --- | --- | --- | --- | --- | --- |
| Light Gas | 2179 | 2179 | 0 | 0 | 0 |
| Benzene | 7464 | 0 | 7389 | 75 | 0 |
| Toluene | 1572 | 0 | 1556 | 16 | 0 |
| EB | 3535 | 0 | 0 | 3500 | 35 |
| OX | 46510 | 0 | 0 | 46045 | 465 |

TABLE 4-continued

Modeling Data for Comparative Example
1 (all mass flows provided in Kg/hr)

| | | | | | |
|---|---|---|---|---|---|
| MX | 103252 | 0 | 0 | 102219 | 1033 |
| PX | 45921 | 0 | 0 | 45461 | 459 |
| C$_9$ aromatics | 2030 | 0 | 0 | 0 | 2030 |
| Total Mass Flow | 212463 | 2179 | 8946 | 197315 | 4023 |

Example 2: System 100 for Producing PX Illustrated in FIG. 2

For Example 2, the system 100 for producing PX illustrated in FIG. 2 and described in conjunction with FIG. 2 is modeled based on the assumptions previously described at the beginning of the Examples section. For Example 2, the xylene-containing effluent 22 is passed from the xylene rerun column 20 to the PX-recovery unit 110, the PX-depleted effluent 114 is passed directly from the PX-recovery unit 110 to the membrane isomerization unit 120, and the EB dealkylation unit 130, stripper 150, and membrane separation unit 140 (in that order) are disposed downstream of the membrane isomerization unit 120. The permeate 142 from the membrane separation unit 140 is recycled back to the PX-recovery unit 110, and the retentate 144 from the membrane separation unit 140 is passed back to the membrane isomerization unit 120. The modeling results in the form of the mass flow rates of each constituent in each process stream of Example 2 (FIG. 2) are shown in Table 5, which is provided subsequently in this disclosure. The mass flow rates are rounded to the nearest Kg/hr.

TABLE 5

Modeling Data for Example 2 (all mass flow rates provided in Kg/hr)

| Stream # | 12 | 24 | 22 | 146 | 112 |
|---|---|---|---|---|---|
| Light Gas | 0 | 0 | 0 | 0 | 0 |
| Benzene | 0 | 0 | 0 | 39 | 0 |
| Toluene | 1328 | 0 | 1328 | 1347 | 0 |
| EB | 8299 | 0 | 8335 | 8475 | 7 |
| OX | 11619 | 0 | 12259 | 14792 | 21 |
| MX | 18922 | 0 | 20692 | 27702 | 43 |
| PX | 8963 | 0 | 9676 | 54836 | 35644 |
| C$_9$ aromatics | 17262 | 19409 | 196 | 196 | 0 |
| Total Mass Flow | 66393 | 19409 | 52485 | 107389 | 35715 |

| Stream # | 114 | 116 | 122 | 132 | 194 |
|---|---|---|---|---|---|
| Light Gas | 0 | 0 | 0 | 2191 | 2191 |
| Benzene | 39 | 62 | 62 | 6162 | 0 |
| Toluene | 1347 | 1358 | 1358 | 3004 | 0 |
| EB | 8468 | 11845 | 11845 | 3554 | 0 |
| OX | 14771 | 75575 | 64755 | 63978 | 0 |
| MX | 27659 | 195899 | 179173 | 177022 | 0 |
| PX | 19193 | 44595 | 72142 | 71276 | 0 |
| C$_9$ aromatics | 196 | 196 | 196 | 2343 | 0 |
| Total Mass Flow | 71674 | 329530 | 329530 | 329530 | 2191 |

| Stream # | 196 | 154 | 156 | 142 | 144 |
|---|---|---|---|---|---|
| Light Gas | 0 | 0 | 0 | 0 | 0 |
| Benzene | 6101 | 62 | 0 | 39 | 22 |
| Toluene | 2974 | 30 | 0 | 19 | 11 |
| EB | 0 | 3518 | 36 | 141 | 3377 |
| OX | 0 | 63338 | 640 | 2534 | 60805 |

TABLE 5-continued

Modeling Data for Example 2 (all mass flow rates provided in Kg/hr)

| | | | | | |
|---|---|---|---|---|---|
| MX | 0 | 175252 | 1770 | 7010 | 168240 |
| PX | 0 | 70564 | 713 | 45160 | 25403 |
| C$_9$ aromatics | 0 | 0 | 2343 | 0 | 0 |
| Total Mass Flow | 9074 | 312764 | 5501 | 54903 | 257857 |

Example 3: System 200 for Producing PX Illustrated in FIG. 3

For Example 3, the system 200 for producing PX illustrated in FIG. 3 and described in conjunction with FIG. 3 is modeled based on the assumptions previously described at the beginning of the Examples section. For Example 3, the xylene-containing effluent 22 is passed from the xylene rerun column 20 to the PX-recovery unit 110, the PX-depleted effluent 114 is passed directly from the PX-recovery unit 110 to the membrane isomerization unit 120, and the membrane separation unit 140 is disposed upstream of the EB dealkylation unit 130 with the stripper 150 downstream of the EB dealkylation unit 130. The permeate 242 from the membrane separation unit 140 is recycled back to the PX-recovery unit 110, and the retentate 244 from the membrane separation unit 140 is passed on to the EB dealkylation unit 130. The EB-depleted effluent 254 from the stripper 150 is recycled back to the membrane isomerization unit 120. The modeling results in the form of the mass flow rates of each constituent in each process stream of Example 3 (FIG. 3) are shown in Table 6, which is provided subsequently in this disclosure. The mass flow rates are rounded to the nearest Kg/hr.

TABLE 6

Modeling Data for Example 3 (all mass flow rates provided in Kg/hr)

| Stream # | 12 | 24 | 22 | 246 | 112 |
|---|---|---|---|---|---|
| Light Gas | 0 | 0 | 0 | 0 | 0 |
| Benzene | 0 | 0 | 0 | 107 | 0 |
| Toluene | 1304 | 0 | 1304 | 3670 | 0 |
| EB | 8151 | 0 | 8302 | 9271 | 7 |
| OX | 11411 | 0 | 12018 | 14577 | 21 |
| MX | 18583 | 0 | 20264 | 27353 | 43 |
| PX | 8803 | 0 | 9057 | 54836 | 35644 |
| C$_9$ aromatics | 16953 | 18701 | 189 | 191 | 0 |
| Total Mass Flow | 65204 | 18701 | 61133 | 110007 | 35715 |

| Stream # | 114 | 216 | 222 | 232 | 294 |
|---|---|---|---|---|---|
| Light Gas | 0 | 0 | 0 | 2152 | 2152 |
| Benzene | 107 | 168 | 168 | 6053 | 0 |
| Toluene | 3570 | 3697 | 3697 | 2671 | 0 |
| EB | 9264 | 24240 | 24240 | 15127 | 0 |
| OX | 14556 | 74644 | 63992 | 60695 | 0 |
| MX | 27310 | 193719 | 177220 | 168090 | 0 |
| PX | 19193 | 44380 | 71530 | 25442 | 0 |
| C$_9$ aromatics | 191 | 191 | 191 | 1937 | 0 |
| Total Mass Flow | 74292 | 341038 | 341038 | 282166 | 2152 |

| Stream # | 296 | 254 | 256 | 242 | 244 |
|---|---|---|---|---|---|
| Light Gas | 0 | 0 | 0 | 0 | 0 |
| Benzene | 5993 | 61 | 0 | 107 | 60 |
| Toluene | 2644 | 27 | 0 | 2366 | 1331 |
| EB | 0 | 14975 | 151 | 970 | 23272 |

TABLE 6-continued

Modeling Data for Example 3 (all mass flow rates provided in Kg/hr)

| | | | | | |
|---|---|---|---|---|---|
| OX | 0 | 60088 | 607 | 2560 | 61432 |
| MX | 0 | 166409 | 1681 | 7089 | 170131 |
| PX | 0 | 25187 | 254 | 45779 | 25751 |
| C$_9$ aromatics | 0 | 0 | 1937 | 2 | 189 |
| Total Mass Flow | 8637 | 266747 | 4630 | 58873 | 282166 |

Example 4: System 300 for Producing PX Illustrated in FIG. 4

In Example 4, the system 300 for producing PX illustrated in FIG. 4 and described in conjunction with FIG. 4 is modeled based on the assumptions previously described at the beginning of the Examples section. For Example 4, the xylene-containing effluent 22 is passed from the xylene rerun column 20 to the PX-recovery unit 110, the PX-depleted effluent 114 is passed directly from the PX-recovery unit 110 to the EB dealkylation unit 130, and the stripper 150, membrane isomerization unit 120, and membrane separation unit 140 (in that order) are disposed downstream of the EB dealkylation unit 130. The permeate 342 from the membrane separation unit 140 is recycled back to the PX-recovery unit 110, and the retentate 344 from the membrane separation unit 140 is recycled back to the EB dealkylation unit 130. The modeling results in the form of the mass flow rates of each constituent in each process stream of Example 4 (FIG. 4) are shown in Table 7, which is provided subsequently in this disclosure. The mass flow rates are rounded to the nearest Kg/hr.

TABLE 7

Modeling Data for Example 4 (all mass flow rates provided in Kg/hr)

| Stream # | 12 | 24 | 22 | 346 | 112 |
|---|---|---|---|---|---|
| Light Gas | 0 | 0 | 0 | 0 | 0 |
| Benzene | 0 | 0 | 0 | 39 | 0 |
| Toluene | 1329 | 0 | 1329 | 1348 | 0 |
| EB | 8305 | 0 | 8340 | 8481 | 7 |
| OX | 11627 | 0 | 12380 | 14933 | 21 |
| MX | 18935 | 0 | 20885 | 27949 | 43 |
| PX | 8969 | 0 | 9411 | 54836 | 35644 |
| C$_9$ aromatics | 17274 | 19436 | 196 | 196 | 0 |
| Total Mass Flow | 66438 | 19436 | 52641 | 107784 | 35715 |

| Stream # | 114 | 316 | 332 | 354 | 394 |
|---|---|---|---|---|---|
| Light Gas | 0 | 0 | 2193 | 0 | 2193 |
| Benzene | 39 | 62 | 6167 | 62 | 0 |
| Toluene | 1348 | 1359 | 3017 | 30 | 0 |
| EB | 8474 | 11854 | 3556 | 3521 | 0 |
| OX | 14912 | 76205 | 75290 | 74537 | 0 |
| MX | 27906 | 197439 | 195069 | 193119 | 0 |
| PX | 19193 | 44744 | 44207 | 43765 | 0 |
| C$_9$ aromatics | 196 | 196 | 2359 | 0 | 0 |
| Total Mass Flow | 72069 | 331858 | 331858 | 315034 | 2193 |

| Stream # | 396 | 322 | 356 | 342 | 344 |
|---|---|---|---|---|---|
| Light Gas | 0 | 0 | 0 | 0 | 0 |
| Benzene | 6105 | 62 | 0 | 39 | 22 |
| Toluene | 2987 | 30 | 0 | 19 | 11 |
| EB | 0 | 3521 | 36 | 141 | 3380 |
| OX | 0 | 63847 | 753 | 2554 | 61293 |

TABLE 7-continued

Modeling Data for Example 4 (all mass flow rates provided in Kg/hr)

| | | | | | |
|---|---|---|---|---|---|
| MX | 0 | 176596 | 1951 | 7064 | 169532 |
| PX | 0 | 70977 | 442 | 45425 | 25552 |
| C$_9$ aromatics | 0 | 0 | 2359 | 0 | 0 |
| Total Mass Flow | 9092 | 315032 | 5540 | 55242 | 259789 |

Example 5: System 400 for Producing PX Illustrated in FIG. 5

In Example 5 the system 400 for producing PX illustrated in FIG. 5 and described in conjunction with FIG. 5 is modeled based on the assumptions previously described at the beginning of the Examples section. For Example 5, the xylene-containing effluent 22 is passed from the xylene rerun column 20 directly to the membrane separation unit 140, the permeate 442 is passed from the membrane separation unit 140 to the PX-recovery unit 110, and the retentate 444 and the PX-depleted effluent 114 are passed to the membrane isomerization unit 120. The EB dealkylation unit 130 and stripper 150 are downstream of the membrane isomerization unit 120, and the EB-depleted effluent 454 is recycled from the stripper 150 back to the membrane separation unit 140. The modeling results in the form of the mass flow rates of each constituent in each process stream of Example 5 (FIG. 5) are shown in Table 8, which is provided subsequently in this disclosure. The mass flow rates are rounded to the nearest Kg/hr.

TABLE 8

Modeling Data for Example 5 (all mass flow rates provided in Kg/hr)

| Stream # | 12 | 24 | 22 | 448 | 112 |
|---|---|---|---|---|---|
| Light Gas | 0 | 0 | 0 | 0 | 0 |
| Benzene | 1334 | 0 | 1334 | 1410 | 0 |
| Toluene | 0 | 0 | 0 | 17 | 0 |
| EB | 8337 | 0 | 8373 | 11908 | 7 |
| OX | 11672 | 0 | 12335 | 78069 | 21 |
| MX | 19009 | 0 | 20855 | 203598 | 43 |
| PX | 9004 | 0 | 9771 | 85682 | 35644 |
| C$_9$ aromatics | 17342 | 19595 | 0 | 0 | 0 |
| Total Mass Flow | 66699 | 19595 | 52670 | 380685 | 35715 |

| Stream # | 114 | 418 | 422 | 432 | 494 |
|---|---|---|---|---|---|
| Light Gas | 0 | 0 | 0 | 2201 | 2201 |
| Benzene | 902 | 1410 | 1410 | 7539 | 0 |
| Toluene | 11 | 17 | 17 | 1744 | 0 |
| EB | 469 | 11901 | 11901 | 3570 | 0 |
| OX | 3101 | 78048 | 67202 | 66396 | 0 |
| MX | 8101 | 203556 | 186836 | 184594 | 0 |
| PX | 19193 | 50038 | 77602 | 76671 | 0 |
| C$_9$ aromatics | 0 | 0 | 0 | 2253 | 0 |
| Total Mass Flow | 31778 | 344970 | 344970 | 344970 | 2201 |

| Stream # | 496 | 454 | 456 | 442 | 444 |
|---|---|---|---|---|---|
| Light Gas | 0 | 0 | 0 | 0 | 0 |
| Benzene | 7464 | 76 | 0 | 902 | 508 |
| Toluene | 1727 | 17 | 0 | 11 | 6 |
| EB | 0 | 3535 | 36 | 476 | 11432 |
| OX | 0 | 65732 | 664 | 3123 | 74947 |
| MX | 0 | 182748 | 1846 | 8144 | 195454 |

TABLE 8-continued

| Modeling Data for Example 5 (all mass flow rates provided in Kg/hr) | | | | | |
|---|---|---|---|---|---|
| PX | 0 | 75911 | 767 | 54836 | 30845 |
| C$_9$ aromatics | 0 | 0 | 2253 | 0 | 0 |
| Total Mass Flow | 9191 | 328015 | 5565 | 67493 | 313192 |

Example 6: System 500 for Producing PX Illustrated in FIG. 6

In Example 6 the system 500 for producing PX illustrated in FIG. 6 and described in conjunction with FIG. 6 is modeled based on the assumptions previously described at the beginning of the Examples section. For Example 6, the xylene-containing effluent 22 is passed from the xylene rerun column 20 directly to the membrane separation unit 140, the permeate 542 is passed from the membrane separation unit 140 to the PX-recovery unit 110, and the retentate 544 and the PX-depleted effluent 114 are passed to the EB dealkylation unit 130. The stripper 150 and membrane isomerization unit 120 (in that order) are downstream of the EB dealkylation unit 130, and the isomerate 522 is recycled from the membrane isomerization unit 120 back to the membrane separation unit 140. The modeling results in the form of the mass flow rates of each constituent in each process stream of Example 6 (FIG. 6) are shown in Table 9, which is provided subsequently in this disclosure. The mass flow rates are rounded to the nearest Kg/hr.

TABLE 9

| Modeling Data for Example 6 (all mass flow rates provided in Kg/hr) | | | | | |
|---|---|---|---|---|---|
| Stream # | 12 | 24 | 22 | 548 | 112 |
| Light Gas | 0 | 0 | 0 | 0 | 0 |
| Benzene | 1335 | 0 | 1335 | 1410 | 0 |
| Toluene | 0 | 0 | 0 | 18 | 0 |
| EB | 8343 | 0 | 8379 | 11915 | 7 |
| OX | 11680 | 0 | 12456 | 78634 | 21 |
| MX | 19021 | 0 | 21046 | 204950 | 43 |
| PX | 9010 | 0 | 9504 | 85682 | 35644 |
| C$_9$ aromatics | 17353 | 19618 | 0 | 0 | 0 |
| Total Mass Flow | 66741 | 19618 | 52720 | 382608 | 35715 |

TABLE 9-continued

| Modeling Data for Example 6 (all mass flow rates provided in Kg/hr) | | | | | |
|---|---|---|---|---|---|
| Stream # | 114 | 518 | 532 | 554 | 594 |
| Light Gas | 0 | 0 | 2203 | 0 | 2203 |
| Benzene | 903 | 1410 | 7543 | 75 | 0 |
| Toluene | 11 | 18 | 1754 | 18 | 0 |
| EB | 469 | 11908 | 3572 | 3536 | 0 |
| OX | 3124 | 78613 | 77670 | 76893 | 0 |
| MX | 8155 | 204907 | 202448 | 200423 | 0 |
| PX | 19193 | 50038 | 49438 | 48943 | 0 |
| C$_9$ aromatics | 0 | 0 | 2266 | 0 | 0 |
| Total Mass Flow | 31855 | 346893 | 346893 | 329889 | 2203 |
| Stream # | 596 | 522 | 556 | 542 | 544 |
| Light Gas | 0 | 0 | 0 | 0 | 0 |
| Benzene | 7468 | 75 | 0 | 903 | 508 |
| Toluene | 1737 | 18 | 0 | 11 | 6 |
| EB | 0 | 3536 | 36 | 477 | 11438 |
| OX | 0 | 66178 | 777 | 3145 | 75489 |
| MX | 0 | 183904 | 2024 | 8189 | 196752 |
| PX | 0 | 76178 | 494 | 54836 | 30845 |
| C$_9$ aromatics | 0 | 0 | 2266 | 0 | 0 |
| Total Mass Flow | 9205 | 329889 | 5597 | 67570 | 315038 |

Example 7: Comparison of the Examples 2-6 to Comparative Example 1

In Example 7, the processes of Examples 2-6 are compared to the process of Comparative Example 1 with respect to the relative feed rates to and size factors of the PX recovery units (PX-recovery unit 30 in FIG. 1 and PX-recovery unit 110 in FIGS. 2, 3, and 5) and the strippers (stripper 50 in FIG. 1 and stripper 150 in FIGS. 2, 3, and 5). Table 10, which is provided subsequently in this disclosure, provides the feed rates to the xylene rerun column, the PX-recovery unit, and the stripper for each of the processes of Comparative Example 1 and Examples 2, 3, and 5 at the fixed production rate of PX, which is equivalent to 300 kilotons per annum (KTA). Additionally, size factors for each of the xylene rerun column, PX-recovery unit, and stripper for each of Examples 2-6 were calculated by dividing the feed rate to the unit of the Example by the feed rate to the corresponding unit of the process of Comparative Example 1. For example, the size factor for the PX-recovery unit of Example 2 is calculated by dividing the feed rate to the PX-recovery unit of Example 2 by the feed rate to the PX-recovery unit of Comparative Example 1.

TABLE 10

| Comparison of Examples 2-6 to Comparative Example 1 | | | | | | |
|---|---|---|---|---|---|---|
| | Comparative Example 1 | Ex. 2 | Ex. 3 | Ex. 4 | Ex. 5 | Ex. 6 |
| FIG. Reference | 1 | 2 | 3 | 4 | 5 | 6 |
| Stream No. for Fresh Feed to Xylene Rerun Col. | 32 | 112 | 112 | 112 | 112 | 112 |
| Stream No. for Feed to PX-Recovery Unit | 26 | 146 | 246 | 346 | 442 | 442 |
| Stream No. for Feed to Stripper | 42 | 132 | 232 | 332 | 432 | 532 |
| PX Production Rate (KTA) | 300 | 300 | 300 | 300 | 300 | 300 |
| Fresh Feed Rate to Xylene Rerun Col. (kg/hr) | 66042 | 66393 | 65204 | 66438 | 66699 | 66741 |

TABLE 10-continued

Comparison of Examples 2-6 to Comparative Example 1

|  | Comparative Example 1 | Ex. 2 | Ex. 3 | Ex. 4 | Ex. 5 | Ex. 6 |
| --- | --- | --- | --- | --- | --- | --- |
| Size Factor for Xylene Rerun Col. | 1.00 | 1.01 | 0.99 | 1.01 | 1.01 | 1.01 |
| Feed Rate to PX-Recovery Unit (kg/hr) | 248178 | 107389 | 110007 | 107784 | 67493 | 67570 |
| Size Factor for PX-Recovery Unit | 1.00 | 0.43 | 0.44 | 0.43 | 0.27 | 0.27 |
| Feed Rate to Stripper (kg/hr) | 212463 | 329530 | 270529 | 331858 | 344970 | 346893 |
| Size Factor for Stripper | 1.00 | 1.55 | 1.27 | 1.56 | 1.62 | 1.63 |

As shown in Table 10, the processes of Examples 2-6 that include the PX-recovery unit 110 in combination with the membrane isomerization unit 120, EB dealkylation unit 130, membrane separation unit 140, and stripper 150 resulted in a reduced size factor for the PX-recovery unit compared to the size of the PX recovery unit required to achieve the same PX production rate with the process of Comparative Example 1. For Examples 5 and 6, passing the xylene-containing stream 22 from the xylene rerun column 20 to the membrane separation unit 140 upstream of the PX-recovery unit 110 further reduced the size of the PX-recovery unit 110 from a size factor of 0.43 to 0.27 compared to Examples 2-4. Thus, the data for Examples 2-6 in comparison to Comparative Example 1 shows that incorporating the membrane isomerization unit 120, the EB dealkylation unit 130, and the stripper 150 into the process for producing PX can reduce the size of the PX-recovery unit 110 to produce the same production rate of PX compared to existing PX production processes.

In a first aspect of the present disclosure, a method for producing para-xylene (PX) may include separating a $C_8$ aromatic-containing composition into a xylene-containing effluent and a heavy effluent, the xylene-containing effluent comprising p-xylene (PX), ethylbenzene (EB), and one or both of m-xylene (MX) and o-xylene (OX). The method may further include isomerizing at least a portion of the MX, the OX, or both from the xylene-containing effluent to PX by contacting the portion of the MX, OX, or both with a catalytic membrane in a membrane isomerization unit, dealkylating at least a portion of the EB in the xylene-containing composition to form one or more $C_{7-}$ compounds, subjecting at least a portion of the xylene-containing composition to a membrane separation unit to produce a permeate that is PX-rich and a retentate that is PX-lean, and recovering PX from the xylene-containing composition, the permeate, or both in a PX recovery unit to produce a PX product.

A second aspect of the present disclosure may include the first aspect, in which the membrane separation unit comprises a carbon-based membrane.

A third aspect of the present disclosure may include either the first or second aspect, in which the membrane isomerization unit comprises an acidic sulfonated catalytic membrane.

A fourth aspect of the present disclosure may include any of the first through third aspects, further comprising subjecting at least a second portion of the xylene-containing composition to a separation process operable to separate at least a portion of the $C_{7-}$ compounds from the at least a second portion of the xylene-containing composition.

A fifth aspect of the present disclosure may include the fourth aspect, in which separating the $C_{7-}$ compounds from the at least the second portion of the xylene-containing composition comprises passing the second portion of the xylene-containing composition to a stripper.

A sixth aspect of the present disclosure may include any of the first through fifth aspects, in which dealkylating the at least a portion of the EB comprises contacting the at least a portion of the EB with a dealkylation catalyst in an EB dealkylation unit.

A seventh aspect of the present disclosure may include any of the first through sixth aspects, in which recovering PX includes subjecting at least a third portion of the xylene-containing composition to crystallization, selective adsorption, or combinations of these to recover the PX product.

An eighth aspect of the present disclosure may include any of the first through seventh aspects, in which the PX product comprises at least 99.0 weight percent PX.

In a ninth aspect of the present disclosure, a method for producing p-xylene from a $C_8$-aromatic-containing composition may include introducing a $C_8$ aromatic-containing composition to a xylene rerun column operable to separate the $C_8$ aromatic-containing composition into a xylene-containing effluent and a heavy effluent, the xylene-containing effluent comprising p-xylene (PX) and at least one of m-xylene (MX), o-xylene (OX), ethylbenzene (EB), or combinations of these. The method may further include passing the xylene-containing effluent to a PX processing loop that includes a PX recovery unit operable to separate at least a PX product stream from at least a portion of the xylene-containing effluent, a membrane isomerization unit operable to convert at least a portion of the MX, OX, or both from the xylene-containing effluent to PX, an EB dealkylation unit operable to dealkylate EB from the xylene-containing effluent to produce benzene, toluene, other $C_{7-}$ compounds, or combinations of these, and a membrane separation unit operable to produce a permeate that is PX-rich and a retentate that is PX-lean. The method may further include passing the PX product stream out of PX processing loop.

A tenth aspect of the present disclosure may include the ninth aspect, in which the xylene isomerization loop further comprises a stripper disposed immediately downstream of the EB dealkylation unit, the stripper operable to remove at least a portion of the one or more $C_{7-}$ hydrocarbon compounds from the xylene isomerization loop.

An eleventh aspect of the present disclosure may include the tenth aspect, in which the method further includes passing a dealkylation effluent from the EB dealkylation unit to the stripper, the dealkylation effluent comprising the one or more $C_{7-}$ compounds, and passing a $C_{7-}$ effluent out of the stripper, the $C_{7-}$ effluent comprising at least a portion of the $C_{7-}$ compounds from the dealkylation effluent, where passing the $C_{7-}$ effluent out of the stripper removes the at least a portion of the $C_{7-}$ compounds from the xylene isomerization loop.

A twelfth aspect of the present disclosure may include either of the tenth or eleventh aspects, further comprising passing a stripper bottoms effluent back to the xylene rerun column.

A thirteenth aspect of the present disclosure may include any of the ninth through twelfth aspects, in which passing the xylene-containing effluent to a PX processing loop includes passing at least a portion of the xylene-containing effluent to the PX recovery unit to separate the at least a portion of the xylene-containing effluent into a PX product and a PX-depleted effluent, recovering the PX product from the PX recovery unit, passing the PX-depleted effluent through a xylene isomerization loop, the xylene isomerization loop comprising at least the membrane isomerization unit, the EB dealkylation unit, and the membrane separation unit, passing the permeate back to the PX recovery unit, and passing the retentate back through the xylene isomerization loop.

A fourteenth aspect of the present disclosure may include the thirteenth aspect, in which the ethylbenzene dealkylation unit is disposed downstream of the membrane isomerization unit.

A fifteenth aspect of the present disclosure may include either of the thirteenth or fourteenth aspects, in which passing the PX-depleted effluent through the xylene isomerization loop includes passing the PX-depleted effluent from the PX recovery unit directly to the membrane isomerization unit, and passing the PX-depleted effluent through a catalytic membrane in the membrane isomerization unit, which causes isomerization of at least a portion of the MX, OX, EB, or combinations of these in the PX-depleted effluent to PX to produce an isomerate having a concentration of PX greater than a concentration of PX in the PX-depleted effluent.

A sixteenth aspect of the present disclosure may include the fifteenth aspect, further comprising passing the isomerate from the membrane isomerization unit to the EB dealkylation unit, and contacting the isomerate with a dealkylation catalyst, which causes dealkylation of at least a portion of the EB in the isomerate to produce a dealkylation effluent comprising the one or more $C_{7-}$ compounds and having a concentration of EB less than a concentration of EB in the isomerate.

A seventeenth aspect of the present disclosure may include any of the thirteenth through sixteenth aspects, further comprising passing the dealkylation effluent to a stripper operable to separate the dealkylation effluent into a $C_{7-}$ effluent and an EB-depleted effluent, passing the $C_{7-}$ effluent out of the stripper, the $C_{7-}$ effluent comprising at least a portion of the $C_{7-}$ compounds from the dealkylation effluent, and passing the EB-depleted effluent out of the stripper, the EB-depleted effluent having a concentration of EB less than the concentration of EB in the isomerate.

An eighteenth aspect of the present disclosure may include the seventeenth aspect, further comprising passing the EB-depleted effluent to the membrane separation unit, passing the EB-depleted effluent through a carbon-based membrane, which causes separation of the EB-depleted effluent into the permeate and the retentate, and passing the retentate back to the membrane isomerization unit.

A nineteenth aspect of the present disclosure may include any of the thirteenth through fifteenth aspects, further comprising passing the isomerate from the membrane isomerization unit to the membrane separation unit, and passing the isomerate through a carbon-based membrane, which causes separation of the isomerate into the permeate and the retentate, the permeate having a concentration of PX greater than the concentration of PX in the retentate.

A twentieth aspect of the present disclosure may include the nineteenth aspect, further comprising passing the retentate to the EB dealkylation unit, and contacting the retentate with a dealkylation catalyst, which causes dealkylation of at least a portion of the EB in the retentate to produce a dealkylation effluent comprising the one or more $C_{7-}$ hydrocarbon compounds and having a concentration of EB less than a concentration of EB in the retentate.

A twenty-first aspect of the present disclosure may include the twentieth aspect, further comprising passing the dealkylation effluent to the stripper operable to separate the dealkylation effluent into a $C_{7-}$ effluent and an EB-depleted effluent, passing the $C_{7-}$ effluent out of the stripper, the $C_{7-}$ effluent comprising at least a portion of the $C_{7-}$ compounds from the dealkylation effluent, and passing the EB-depleted effluent from the stripper back to the membrane isomerization unit.

A twenty-second aspect of the present disclosure may include any of the ninth through thirteenth aspects, further comprising passing the PX-depleted effluent from the PX recovery unit directly to the EB dealkylation unit, and contacting the PX-depleted effluent with a dealkylation catalyst, which causes dealkylation of at least a portion of the EB in the PX-depleted effluent to produce a dealkylation effluent comprising the one or more $C_{7-}$ compounds and having a concentration of EB less than a concentration of EB in the PX-depleted effluent.

A twenty-third aspect of the present disclosure may include the twenty-second aspect, further comprising passing the dealkylation effluent to a stripper operable to separate the dealkylation effluent into a $C_{7-}$ effluent and an EB-depleted effluent, passing the $C_{7-}$ effluent out of the stripper, the $C_{7-}$ effluent comprising at least a portion of the $C_{7-}$ compounds from the dealkylation effluent, and passing the EB-depleted effluent from the stripper to the membrane isomerization unit.

A twenty-fourth aspect of the present disclosure may include the twenty-third aspect, further comprising passing the EB-depleted effluent through a catalytic membrane in the membrane isomerization unit, which causes isomerization of at least a portion of the MX, OX, EB, or combinations of these in the EB-depleted effluent to PX to produce an isomerate having a concentration of PX greater than a concentration of PX in the EB-depleted stream.

A twenty-fifth aspect of the present disclosure may include the twenty-fourth aspect, passing the isomerate to the membrane separation unit, passing the isomerate through a carbon-based membrane in the membrane separation unit, which causes separation of the isomerate into the permeate and the retentate, passing the permeate to the PX recovery unit, and passing the retentate back to the EB dealkylation unit.

A twenty-sixth aspect of the present disclosure may include any of the ninth through twelfth aspects, in which passing the xylene-containing effluent to a PX processing loop comprises passing the xylene-containing effluent to the membrane separation unit operable to separate the xylene-containing effluent into a permeate and a retentate, where the permeate is PX rich and the retentate is PX-lean, and passing the permeate to the PX recovery unit to separate the permeate into the PX product and a PX-depleted effluent.

A twenty-seventh aspect of the present disclosure may include the twenty-sixth aspect, further comprising passing the PX-depleted effluent and the retentate directly to the membrane isomerization unit, and passing the PX-depleted effluent and the retentate through a catalytic membrane in the membrane isomerization unit, which causes isomerization of at least a portion of the MX, OX, EB, or combinations of these in the PX-depleted effluent, the retentate, or both to PX to produce an isomerate having a concentration of PX greater than a concentration of PX in the PX-depleted effluent, the retentate, or a combination of both.

A twenty-eighth aspect of the present disclosure may include the twenty-seventh aspect, further comprising passing the isomerate from the membrane isomerization unit to the EB dealkylation unit, and contacting the isomerate with a dealkylation catalyst, which causes dealkylation of at least a portion of the EB in the isomerate to produce a dealkylation effluent comprising the one or more $C_{7-}$ compounds and having a concentration of EB less than a concentration of EB in the isomerate.

A twenty-ninth aspect of the present disclosure may include the twenty-eighth aspect, further comprising passing the dealkylation effluent to a stripper operable to separate the dealkylation effluent into at least a $C_{7-}$ effluent and an EB-depleted effluent, passing the $C_{7-}$ effluent out of the stripper, the $C_{7-}$ effluent comprising at least a portion of the $C_{7-}$ compounds from the dealkylation effluent, and passing the EB-depleted effluent from the stripper to the membrane separation unit, the EB-depleted effluent having a concentration of EB less than the concentration of EB in the isomerate.

A thirtieth aspect of the present disclosure may include the twenty-sixth aspect, further comprising passing the PX-depleted effluent and the retentate directly to the EB dealkylation unit, and contacting the PX-depleted effluent and the retentate with a dealkylation catalyst, which causes dealkylation of at least a portion of the EB in the PX-depleted effluent, the retentate, or both to produce a dealkylation effluent comprising the one or more $C_{7-}$ compounds and having a concentration of EB less than a total concentration of EB in the PX-depleted effluent, the retentate, or a combination of both.

A thirty-first aspect of the present disclosure may include the thirtieth aspect, further comprising passing the dealkylation effluent to a stripper operable to separate the dealkylation effluent into at least a $C_{7-}$ effluent and an EB-depleted effluent, passing the $C_{7-}$ effluent out of the stripper, the $C_{7-}$ effluent comprising at least a portion of the $C_{7-}$ compounds from the dealkylation effluent, and passing the EB-deleted effluent out of the stripper, the EB-depleted effluent having a concentration of EB less than the total concentration of EB in the combination of the PX-depleted effluent and the retentate.

A thirty-second aspect of the present disclosure may include the thirty-first aspect, further comprising passing the EB-depleted effluent from the stripper to the membrane isomerization unit, passing the EB-depleted effluent through a catalytic membrane in the membrane isomerization unit, which causes isomerization of at least a portion of the MX, OX, EB, or combinations of these in the EB-depleted effluent to PX to produce an isomerate having a concentration of PX greater than a concentration of PX in the EB-depleted stream, and passing the isomerate back to the membrane separation unit.

In a thirty-third aspect of the present disclosure, a system for producing para-xylene (PX) from a $C_8$ aromatic-containing composition may include a xylene rerun column operable to separate the $C_8$ aromatic-containing composition into a xylene-containing effluent and a heavy effluent, the xylene-containing effluent comprising at least PX and one or more of ortho-xylene (OX), meta-xylene (MX), ethylbenzene (EB), or combinations of these. The system may also include a xylene processing loop comprising a PX recovery unit operable to separate the xylene-containing effluent into at least a PX product and a PX-depleted effluent, a membrane isomerization unit operable to convert at least a portion of the MX, OX, EB, or combinations of these from the xylene-containing effluent to PX, an ethylbenzene dealkylation unit operable to dealkylate at least a portion of the EB from the xylene-containing effluent to produce one or more $C_{7-}$ compounds, and a membrane separation unit operable to separate at least a portion of the xylene-containing stream into a permeate that is PX-rich and a retentate that is PX-lean.

A thirty-fourth aspect of the present disclosure may include the thirty-third aspect, further comprising a stripper disposed directly downstream of the EB dealkylation unit, the stripper operable to remove at least a portion of the one or more $C_{7-}$ compounds from the xylene processing loop.

A thirty-fifth aspect of the present disclosure may include either of the thirty-third or thirty-fourth aspects, in which the membrane isomerization unit comprises an acidic sulfonated catalytic membrane.

A thirty-sixth aspect of the present disclosure may include any of the thirty-third through thirty-fifth aspects, in which the membrane separation unit comprises a carbon-based membrane.

A thirty-seventh aspect of the present disclosure may include any of the thirty-third through thirty-sixth aspects, in which the PX-recovery unit is directly downstream of the xylene rerun column so that the xylene-containing effluent passes directly from the xylene rerun column to the PX recovery unit.

A thirty-eighth aspect of the present disclosure may include any of the thirty-third through thirty-seventh aspects, in which the membrane isomerization unit is directly downstream of the PX recovery unit so that the PX-depleted effluent passes directly from the PX recovery unit to the membrane isomerization unit.

A thirty-ninth aspect of the present disclosure may include any of the thirty-third through thirty-eighth aspects, in which the EB dealkylation unit is downstream of the membrane isomerization unit, the membrane separation unit is downstream of the EB dealkylation unit, the permeate is recycled back to the PX recovery unit, and the retentate is recycled back to the membrane isomerization unit.

A fortieth aspect of the present disclosure may include any of the thirty-third through thirty-eighth aspects, in which the membrane separation unit is downstream of the membrane isomerization unit and the EB dealkylation unit is downstream of the membrane separation unit so that the retentate passes directly from the membrane separation unit to the EB dealkylation unit, wherein the permeate is recycled back to the PX recovery unit.

A forty-first aspect of the present disclosure may include any of the thirty-third through thirty-seventh aspects, in which the EB dealkylation unit is directly downstream of the PX recovery unit and the membrane isomerization unit and membrane separation unit are both downstream of the EB dealkylation unit.

A forty-second aspect of the present disclosure may include any of the thirty-third through thirty-sixth aspects, in which the membrane separation unit is downstream of the xylene rerun column and the PX recovery unit, the membrane isomerization unit, and the EB dealkylation unit are downstream of the membrane separation unit.

A forty-third aspect of the present disclosure may include the forty-second aspect, in which the EB dealkylation unit is downstream of the membrane isomerization unit.

A forty-fourth aspect of the present disclosure may include the forty-second aspect, in which the membrane isomerization unit is downstream of the EB dealkylation unit.

It should now be understood that various aspects of the methods and systems for producing PX from $C_8$-containing compositions are described and such aspects may be utilized in conjunction with various other aspects.

Throughout this disclosure ranges are provided for various processing parameters and operating conditions for the systems and methods for producing p-xylene from $C_8$-containing compositions. It will be appreciated that when one or more explicit ranges are provided the individual values and the sub-ranges formed within the range are also intended to be provided as providing an explicit listing of all possible combinations is prohibitive. For example, a provided range of 1-10 also includes the individual values, such as 1, 2, 3, 4.2, and 6.8, as well as all the ranges which may be formed within the provided bounds, such as 1-8, 2-4, 6-9, and 1.3-5.6.

It should be apparent to those skilled in the art that various modifications and variations can be made to the described embodiments without departing from the spirit and scope of the claimed subject matter. Thus, it is intended that the specification cover the modifications and variations of the various described embodiments provided such modifications and variations come within the scope of the appended claims and their equivalents.

What is claimed is:

1. A system for producing para-xylene (PX) from a $C_8$ aromatic-containing composition, the system comprising:
    a xylene rerun column operable to separate the $C_8$ aromatic-containing composition into a xylene-containing effluent and a heavy effluent, the xylene-containing effluent comprising at least PX and one or more of ortho-xylene (OX), meta-xylene (MX), ethylbenzene (EB), or combinations of these;
    a xylene processing loop comprising:
        a PX recovery unit operable to separate the xylene-containing effluent into at least a PX product and a PX-depleted effluent;
        an ethylbenzene dealkylation unit directly downstream of the PX recovery unit so that the PX-depleted effluent passes directly from the PX recovery unit to the ethylbenzene dealkylation unit, and operable to dealkylate at least a portion of the EB from the PX-depleted effluent to produce a dealkylation effluent comprising one or more $C_{7-}$ compounds;
        a stripper disposed directly downstream of the ethylbenzene dealkylation unit, the stripper operable to separate the dealkylation effluent into a $C_{7-}$ effluent, an EB-depleted effluent, and a stripper bottoms;
        a membrane isomerization unit disposed downstream of the stripper and operable to receive the EB-depleted effluent from the stripper and convert at least a portion of the MX, OX, EB, or combinations of these, in the EB-depleted effluent to PX to produce an isomerate; and
        a membrane separation unit operable to separate the isomerate into a permeate that is PX-rich and a retentate that is PX-lean;
    where the stripper is fluidly coupled to the xylene rerun column to recycle the stripper bottoms back to the xylene rerun column.

2. The system of claim 1, in which the membrane isomerization unit comprises an acidic sulfonated catalytic membrane.

3. The system of claim 1, in which the membrane separation unit comprises a carbon-based membrane.

4. The system of claim 1, in which the PX-recovery unit is directly downstream of the xylene rerun column so that the xylene-containing effluent passes directly from the xylene rerun column to the PX recovery unit.

5. The system of claim 1, in which the membrane separation unit is downstream of the xylene rerun column, and in which the PX recovery unit, the EB dealkylation unit, and the membrane isomerization unit are downstream of the membrane separation unit.

6. The system of claim 1, in which the membrane separation unit is directly downstream of the membrane isomerization unit.

7. The system of claim 1, where the EB-depleted effluent from the stripper is in fluid communication with the membrane isomerization unit to pass the EB-depleted effluent from the stripper to membrane isomerization unit.

8. The system of claim 1, where the permeate from the membrane separation unit is in fluid communication with the PX recovery unit to pass the permeate from the membrane separation unit to the PX recovery unit.

9. The system of claim 1, where the permeate from the membrane separation unit is in fluid communication with the xylene-containing effluent to combine the permeate with the xylene-containing effluent upstream of the PX-recovery unit.

10. The system of claim 1, where the retentate is in fluid communication with the ethylbenzene dealkylation unit to pass the retentate from the membrane separation unit directly to the ethylbenzene dealkylation unit.

11. The system of claim 1, where the retentate is in fluid communication with the PX-depleted effluent to combine the retentate with the PX-depleted effluent upstream of the ethylbenzene dealkylation unit.

12. The system of claim 1, where the membrane separation unit is directly downstream of the xylene rerun column and the PX-recovery unit is directly downstream of the membrane separation unit.

13. The system of claim 12, where:
    the membrane separation unit is in fluid communication with the xylene rerun column to pass the xylene-containing effluent directly from the xylene rerun column to the membrane separation unit; and
    the membrane separation unit is in fluid communication with the membrane isomerization unit to pass the isomerate directly from the membrane isomerization unit to the membrane separation unit.

* * * * *